United States Patent
Bofill Herrera et al.

(10) Patent No.: US 11,952,334 B2
(45) Date of Patent: Apr. 9, 2024

(54) COCRYSTALS OF UBIQUINONE AND COMPOSITIONS COMPRISING THEM

(71) Applicant: CENTER FOR INTELLIGENT RESEARCH IN CRYSTAL ENGINEERING, S.L., Palma de Mallorca (ES)

(72) Inventors: Lidia Bofill Herrera, Sant Feliu de Codines (ES); Dafne De Sande Lopez, L'Hospitalet de Llobregat (ES); Rafel Prohens López, Sabadell (ES); Rafael Barbas Cañero, Santa Coloma de Gramenet (ES)

(73) Assignee: CENTER FOR INTELLIGENT RESEARCH IN CRYSTAL ENGINEERING, S.L., Palma de Mallorca (ES)

( * ) Notice: Subject to any disclaimer, the term of this patent is extended or adjusted under 35 U.S.C. 154(b) by 628 days.

(21) Appl. No.: 17/265,327

(22) PCT Filed: Aug. 2, 2019

(86) PCT No.: PCT/EP2019/070856
§ 371 (c)(1),
(2) Date: Feb. 2, 2021

(87) PCT Pub. No.: WO2020/025781
PCT Pub. Date: Feb. 6, 2020

(65) Prior Publication Data
US 2021/0230091 A1    Jul. 29, 2021

(30) Foreign Application Priority Data
Aug. 3, 2018 (EP) .................... 18382590

(51) Int. Cl.
C07C 50/28 (2006.01)
A23L 33/00 (2016.01)
A23L 33/10 (2016.01)
A61K 9/14 (2006.01)

(52) U.S. Cl.
CPC .............. *C07C 50/28* (2013.01); *A23L 33/10* (2016.08); *A23L 33/40* (2016.08); *A61K 9/14* (2013.01); *A23V 2002/00* (2013.01); *C07B 2200/13* (2013.01)

(58) Field of Classification Search
None
See application file for complete search history.

(56) References Cited

U.S. PATENT DOCUMENTS

| | | |
|---|---|---|
| 7,030,102 B1 | 4/2006 | Madhavi et al. |
| 2011/0009424 A1 | 1/2011 | Zhang et al. |
| 2011/0236478 A1 | 9/2011 | Dokou et al. |

FOREIGN PATENT DOCUMENTS

| | | |
|---|---|---|
| EP | 2 417 970 A2 | 2/2012 |
| JP | 2006-183006 A | 7/2006 |
| JP | 2010-537987 A | 12/2010 |
| JP | 2012-501971 A | 1/2012 |
| JP | 2012-522835 A | 9/2012 |
| WO | WO2019/162429 A1 | 8/2019 |

OTHER PUBLICATIONS

Putranti, A. R. et al. "Effectivity and Physicochemical Stability of Nanostructured Lipid Carrier Coenzyme Q10 in Different Ratio of Lipid Cetyl Palmitate and Alpha Tocopheryl Acetate as Carrier" Asian J Pharm Clin Res, vol. 10, Issue 2, 2017, 146-152 (Year: 2017).*
International Search Report for PCT/EP2019/070856 dated Sep. 30, 2019.
Korotkova et al., "Pharmaceutical Cocrystals", Procedia Chemistry, 2014, vol. 10, pp. 473-476.
Written Opinion of the International Searching Authority for PCT/EP2019/070856 dated Sep. 30, 2019.
Cho et al., "Preparation and Characterization of Aripiprazole Cocrystals with Coformers of Multihydroxybenzene Compounds," Crystal Growth & Design, vol. 17, No. 12, 2017, pp. 6641-6652.
Hayashi et al., "Molecular Recognition of Ubiquinone Analogues. Specific Interaction between Quinone and Functional Porphyrin via Multiple Hydrogen Bonds," Journal of the American Chemical Society, vol. 119, No. 31, 1997, pp. 7281-7290.
Japanese Notice of Reasons for Refusal for corresponding Japanese Application No. 2021-529524, dated Jul. 4, 2023, with an English translation.
Takata, "Screening of Cocrystal and its application to drug substance improvement," Pharm Tech Japan, vol. 25, No. 12, 2009, pp. 2543-2554, with an English abstract.

* cited by examiner

*Primary Examiner* — Medhanit W Bahta
(74) *Attorney, Agent, or Firm* — Birch, Stewart, Kolasch & Birch, LLP

(57) ABSTRACT

The present invention relates to a cocrystal of ubiquinone and a hydrogen bond donor coformer, to a process for the preparation thereof, and to its use as a medicament or a dietary supplement. The invention also relates to compositions comprising the cocrystal.

7 Claims, 12 Drawing Sheets

COCRYSTALS OF UBIQUINONE AND COMPOSITIONS COMPRISING THEM

This application claims the benefit of European Patent Application No. 18382590.0 filed Aug. 3, 2018.

TECHNICAL FIELD

The present invention relates to cocrystals of ubiquinone, to processes for the preparation thereof, and to their use as a medicament or a dietary supplement. It also relates to compositions comprising them.

BACKGROUND ART

CoQ-10 (coenzyme Q-10) is a fat-soluble quinone commonly known as ubiquinone. Ubiquinone is found in most living organisms, and is essential for the production of cellular energy. Additionally, it has been found to be effective in cardiovascular diseases and neurodegenerative diseases. Although it can be synthesized in the body, situations may arise when the need for ubiquinone surpasses the body's ability to synthesize it. Ubiquinone can be derived from dietary sources, being often administered in a powdered form, as in a tablet or as a suspension. However, the bioavailability of ubiquinone is limited.

The structure of ubiquinone corresponds to the formula (I):

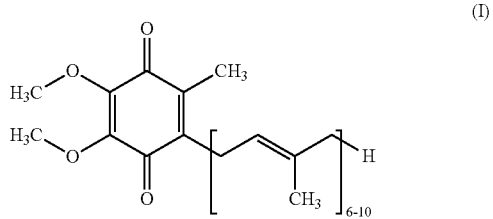

(I)

Ubiquinone is a crystalline powder having a relatively low melting point, mp 50-52° C., and a very low solubility in water, which difficults its bioavailability. In addition, its low melting point determines processing and stability of dosage forms and limits the choice of a suitable form.

A basic requirement for satisfactory bioavailability is that the active ingredient is able to dissolve adequately in the digestive tract. Ubiquinone is usually provided in the pharmaceutical and health food sector in the form of tablets or capsules. Nevertheless, its low solubility still poses some problems regarding to its bioavailability. In order to minimize solubility problems, ubiquinone can be provided as a micronized powder usually in the form of capsules.

It is known that different solid forms of a active ingredient can have different characteristics, and offer certain advantages, for example with regard to solubility or bioavailability. Thus, the discovery of new solid forms allows for improving the pharmacokinetic properties of the active ingredients and as a consequence the characteristics of the pharmaceutical formulations containing the active ingredients, since some forms are more adequate for one type of formulation, and other forms for other different formulations.

Particularly, in recent years cocrystal formation has emerged as a viable strategy towards improving the pharmacokinetic data of active ingredients. By cocrystallizing an active ingredient or a salt of an active ingredient with a coformer (the second component of the cocrystal), a new solid state form of the active ingredient is created having unique properties compared with existing solid forms of the active ingredient or its salts. Such different properties may provide a basis for improving formulation, for example, by facilitating better processing or handling characteristics, changing the dissolution profile in a favourable direction, or improving stability and shelf-life. However, cocrystal formation is not predictable, and in fact is not always possible. Moreover, there is no way to predict the properties of a particular cocrystal of a compound until it is formed. Finding the appropriate coformers and right conditions to obtain a particular cocrystal can take significant time, effort and resources.

Document U.S. Pat. No. 7,030,102B1 discloses a water dispersible freeze-dried CoQ-10/gamma-cyclodextrin complex. The complex is highly bioavailable and thus is useful in the nutritional supplement, oral care, and pharmaceutical industry. Document EP2417970 discloses a coenzyme Q10 nanoparticle binding to an amino acid or protein which is easily absorbed by a human body and has an improved stability.

From what is known in the art, there is still the need of finding new more soluble solid forms of ubiquinone in order to improve the pharmaceutical properties of the pharmaceutical formulations containing them, particularly in terms of bioavailability.

SUMMARY OF INVENTION

The inventors have found that ubiquinone can form a cocrystal with a hydrogen bond donor coformer as defined herein below. The provision of the mentioned cocrystals of ubiquinone gives a new tool to overcome the problems associated with the water solubility of ubiquinone because it has been found that these cocrystals have a better water solubility and higher dissolution rate in aqueous media, what makes them more bioavailable. This property makes the cocrystals more suitable for preparing pharmaceutical or dietary compositions containing ubiquinone.

Cocrystal formation, particularly with a hydrogen bond donor coformer, cannot be predicted. No attempt to obtain cocrystals of ubiquinone has been found in the literature.

Accordingly, the provision of an improved crystal form of ubiquinone in the form of a cocrystal with a hydrogen bond donor coformer as defined herein below is considered a contribution to the art.

Thus, a first aspect of the invention refers to the provision of a cocrystal of ubiquinone and a hydrogen bond donor coformer.

A second aspect of the invention refers to a composition comprising an effective amount of the cocrystal of ubiquinone and a hydrogen bond donor coformer together, with one or more appropriate acceptable excipients or carriers.

Finally, a third aspect of the invention refers to a cocrystal of ubiquinone and a hydrogen bond donor coformer for use as a medicament.

Figure 1:
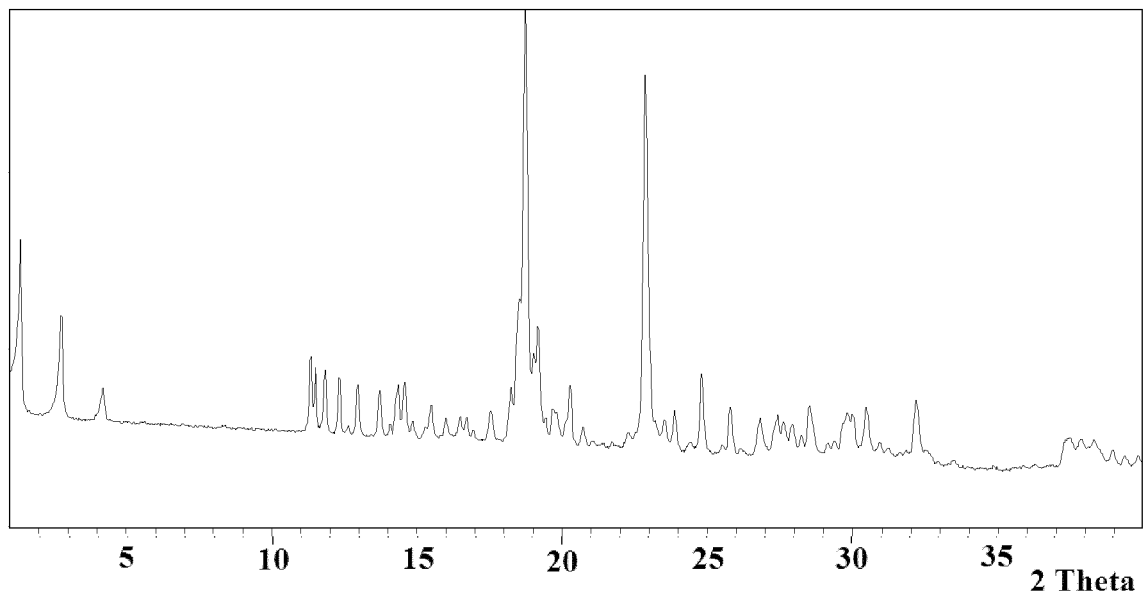
FIG. 1 shows the X-ray powder diffractogram (XRPD) of cocrystal of ubiquinone and 4-hydroxybenzoic acid (1:1).
Figure 2:
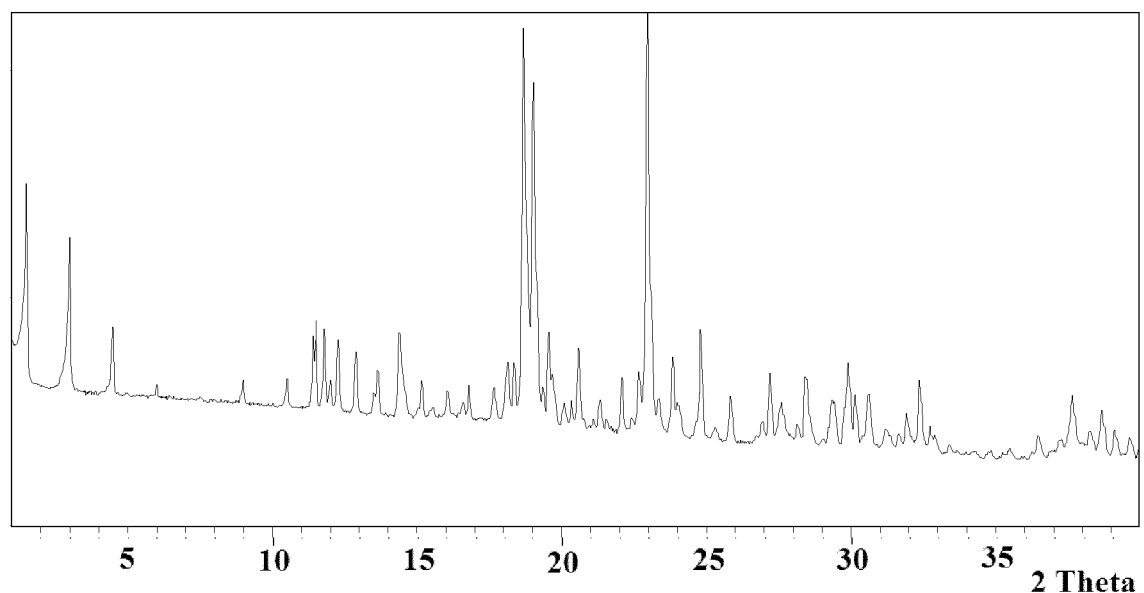
FIG. 2 shows the XRPD of cocrystal of ubiquinone and hydroquinone (2:1).

XRPD diagrams express intensity (I; counts) versus angle 2 theta (°). TGA thermograms express loss weight (% w/w) versus temperature (° C.).

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For the purposes of the present invention, ranges given, such as of temperatures, times, and the like, should be considered approximate, unless specifically stated.

For the purposes of the invention, the term "cocrystal" refers herein to a crystalline entity with at least two different components constituting the unit cell at room temperature (20-25° C.) and interacting by intermolecular interactions. Thus, in a cocrystal, one component crystallizes together with one or more neutral components.

The cocrystals may include one or more solvent molecules in the crystal lattice. Thus, the term "cocrystal hydrate" or "hydrate cocrystal" have the same meaning and are used interchangeable. They refer to a cocrystal including water as a solvent in the crystal lattice. Similarly, cocrystals including other solvents such as benzyl alcohol can be formed.

The expression "cocrystal obtainable by" is used here to define each specific cocrystal of the invention by the process for obtaining it and refers to the product obtainable by any of the corresponding processes disclosed herein. For the purposes of the invention the expressions "obtainable", "obtained" and equivalent expressions are used interchangeably and, in any case, the expression "obtainable" encompasses the expression "obtained".

The term "hydrogen-bond donor coformer" refers to a compound having hydrogen atoms bound to an electronegative atom (such as nitrogen, oxygen, or sulfur) and with the ability to stablish strong intermolecular hydrogen-bonds with a hydrogen-bond acceptor. Examples of hydrogen-bond donor coformers include phosphoric acids, carboxylic acids, alcohols, imidazols, thioamides, sulfinamides, pyrroles, ureas, amides, sulfonamides, and carbamates.

The term "hydrogen-bond acceptor" refers to a compound having at least one electronegative atom (such as oxygen, nitrogen, or halogen) capable of interacting with an electropositive hydrogen atom through a hydrogen bond.

The terms "particle size" and "particle size distribution", as used herein, are in terms of diameter irrespective of the actual particle shape. The term "diameter", as used herein, means the equivalent sphere diameter, namely the diameter of a sphere having the same diffraction pattern, when measured by laser diffraction, as the particle.

As used herein, the term "mean," when used in reference to the size of cocrystal of ubiquinone particles, refers to the sum of the size measurements of all measurable particles measured divided by the total number of particles measured.

As used herein, the term "median," when used in reference to the size of cocrystal of ubiquinone particles, indicates that about 50% of all measurable particles measured have a particle size less than the defined median particle size value, and that about 50% of all measurable particles measured have a particle size greater than the defined median particle size value.

As used herein, the term "mode," when used in reference to the size of cocrystal of ubiquinone particles, indicates the most frequently-occurring particle size value.

As used herein, the term "percent cumulative," when used in reference to the size of cocrystal of ubiquinone particles, refers to an aggregate of the individual percent values for all measurable particles measured at specified diameters.

For particle size distributions, using a volume base calculation, $D_{50}$ is the median value, namely the particle size diameter that splits the distribution with half above and half below this diameter. $D_{90}$ describes the diameter where ninety percent of the distribution has a smaller particle size and ten percent has a larger particle size. Similarly, $D_{10}$ describes the diameter where ten percent of the distribution has a smaller particle size and ninety percent has a larger particle size.

Particle size can be determined, for example by laser dispersion on a Beckman Coulter LS13320 provided with a MLM (Micro Liquid Module) (measure range: 0.4 to 2000 μm; optic model: Fraunhofer.rdf, PIDS included).

When values of characteristic peaks of an X-ray diffractogram are given it is said that these are "approximate" values. It should be understood that the values are the ones shown in the corresponding lists or tables±0.3 degrees 2 theta measured in an X-ray diffractometer with Cu—$K_\alpha$ radiation λ=1.5418 Å.

When a ratio of components of the cocrystals of the invention is specified it refers to the molar ratio of the components that forms the cocrystal. The term "molar ratio" has been used to express the stoichiometric amount in moles of each of the components of a cocrystal. The molar ratio can be determined by $^1$H NMR (Proton nuclear magnetic resonance), thermogravimetric analysis (TGA) or single crystal X-ray diffraction (SCXRD). When values of molar ratio are given according to TGA or $^1$H NMR it is said that these are "approximate" values due to the measurement error. It should be understood that when a molar ratio is mentioned, it corresponds to a molar ratio±0.2%. The variability of the results is due to the inherent sensibility of the TGA or $^1$H NMR equipment.

The term "room temperature" refers to a temperature of the environment, without heating or cooling, and is generally from 20° C. to 25° C.

The term "overnight" refers to a time interval of from 10 h to 20 h.

As used herein, the indefinite articles "a" and "an" are synonymous with "at least one" or "one or more". Unless indicated otherwise, definite articles used herein, such as "the", also include the plural of the noun.

As mentioned above, the first aspect of the invention is the provision of a cocrystal of ubiquinone and a hydrogen bond donor coformer. Also as mentioned above, the cocrystal of the invention may be in crystalline form either as free solvation compound or as a solvate (e.g. a hydrate or a benzyl alcohol solvate) and it is intended that both forms are within the scope of the present invention. Methods of solvation are generally known within the art.

In an embodiment, the hydrogen bond donor coformer is a phenolic compound, particularly an hydroxybenzoic acid.

In another embodiment, the phenolic compound is 4-hydroxybenzoic acid, and the cocrystal of ubiquinone and 4-hydroxybenzoic acid is characterized by having an X-ray powder diffractogram that comprises characteristic peaks at approximately 1.4 and 2.8±0.3 degrees 2 theta (Cu-Kα radiation, λ=1.5418 Å). In a still another embodiment, the cocrystal of ubiquinone and 4-hydroxybenzoic acid of the invention is characterized by having an X-ray powder diffractogram that further comprises characteristic peaks at 13.0, 13.7 and 22.9±0.3 degrees 2 theta (Cu-Kα radiation, λ=1.5418 Å).

In a particular embodiment, the molar ratio of ubiquinone to 4-hydroxybenzoic is 1:1.

More specifically, the cocrystal of ubiquinone and 4-hydroxybenzoic acid of the present disclosure is characterized by exhibiting in the X-ray powder diffractogram a pattern of peaks, expressed in 2 theta units in degrees, 2θ (°), which is shown in Table 1.

TABLE 1

List of selected peaks (only peaks with relative intensity greater than or equal to 1% are indicated):

| Pos. [°2Th.] | Rel. Int. [%] |
|---|---|
| 1.3714 | 27.46 |
| 2.7911 | 13.16 |
| 4.2018 | 3.34 |
| 11.3463 | 7.69 |
| 11.5266 | 6.27 |
| 11.8562 | 5.99 |
| 12.3373 | 5.23 |
| 12.9696 | 4.47 |
| 13.733 | 3.9 |
| 14.371 | 4.6 |
| 14.5922 | 4.81 |
| 18.2385 | 4.62 |
| 18.4655 | 13.88 |
| 18.7549 | 100 |
| 19.1828 | 12.32 |
| 20.2763 | 5.06 |
| 22.8564 | 75.62 |
| 24.8119 | 6.71 |
| 25.8043 | 3.28 |
| 28.5045 | 3.69 |
| 29.8142 | 3.25 |

TABLE 1-continued

List of selected peaks (only peaks with relative intensity greater than or equal to 1% are indicated):

| Pos. [°2Th.] | Rel. Int. [%] |
|---|---|
| 30.4706 | 3.79 |
| 32.1808 | 4.53 |

The cocrystal of ubiquinone and 4-hydroxybenzoic acid of the invention may be further characterized by an X-ray diffractogram as in FIG. 1.

In another embodiment, the phenolic compound is hydroquinone, and the cocrystal of ubiquinone and hydroquinone is characterized by having an X-ray powder diffractogram that comprises characteristic peaks at approximately 1.5 and 3.0±0.3 degrees 2 theta (Cu-Kα radiation, λ=1.5418 Å). In still another embodiment, the cocrystal of ubiquinone and hydroquinone is characterized by having an X-ray powder diffractogram that further comprises characteristic peaks at 12.9, 14.4 and 23.0±0.3 degrees 2 theta (Cu-Kα radiation, λ=1.5418 Å).

In a particular embodiment, the molar ratio of ubiquinone to hydroquinone is 2:1.

More specifically, the cocrystal of ubiquinone and hydroquinone of the present disclosure is characterized by exhibiting in the X-ray powder diffractogram a pattern of peaks, expressed in 2 theta units in degrees, 2θ (°), which is shown in Table 2.

TABLE 2

List of selected peaks (only peaks with relative intensity greater than or equal to 1% are indicated):

| Pos. [°2Th.] | Rel. Int. [%] |
|---|---|
| 1.5052 | 58.69223 |
| 3.0057 | 29.39469 |
| 4.5052 | 19.6141 |
| 11.5238 | 7.67905 |
| 11.8106 | 7.49322 |
| 12.2781 | 7.20895 |
| 12.8979 | 6.86386 |
| 13.6644 | 6.48055 |
| 14.4038 | 6.14946 |
| 18.1459 | 4.88888 |
| 18.3655 | 4.83091 |
| 18.6961 | 4.74623 |
| 19.0292 | 4.66389 |
| 19.569 | 4.53644 |
| 20.6055 | 4.31053 |
| 22.0939 | 4.0234 |
| 22.6733 | 3.92188 |
| 22.9653 | 3.87267 |
| 23.8454 | 3.73169 |
| 24.8219 | 3.58706 |
| 27.2012 | 3.27846 |
| 28.4416 | 3.13824 |
| 29.8979 | 2.98861 |
| 30.1597 | 2.96326 |
| 30.6117 | 2.92053 |
| 32.3657 | 2.76616 |
| 37.6495 | 2.38921 |

Figure 3:
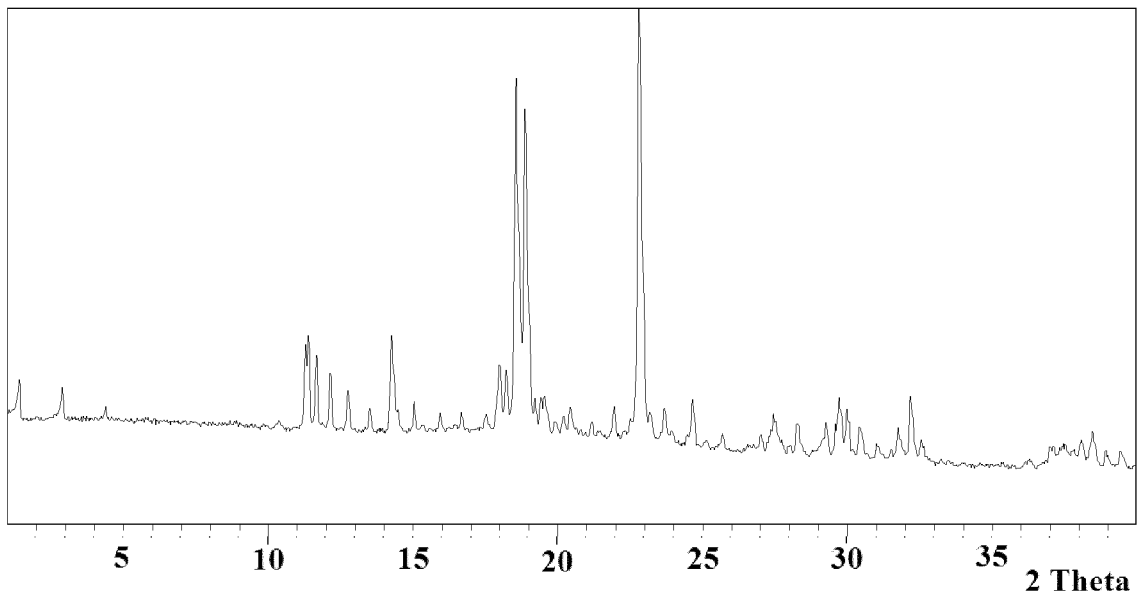
FIG. 3 shows the XRPD of cocrystal of ubiquinone and hydroquinone cocrystal benzyl alcohol solvate (2:1:1).
Figure 4:
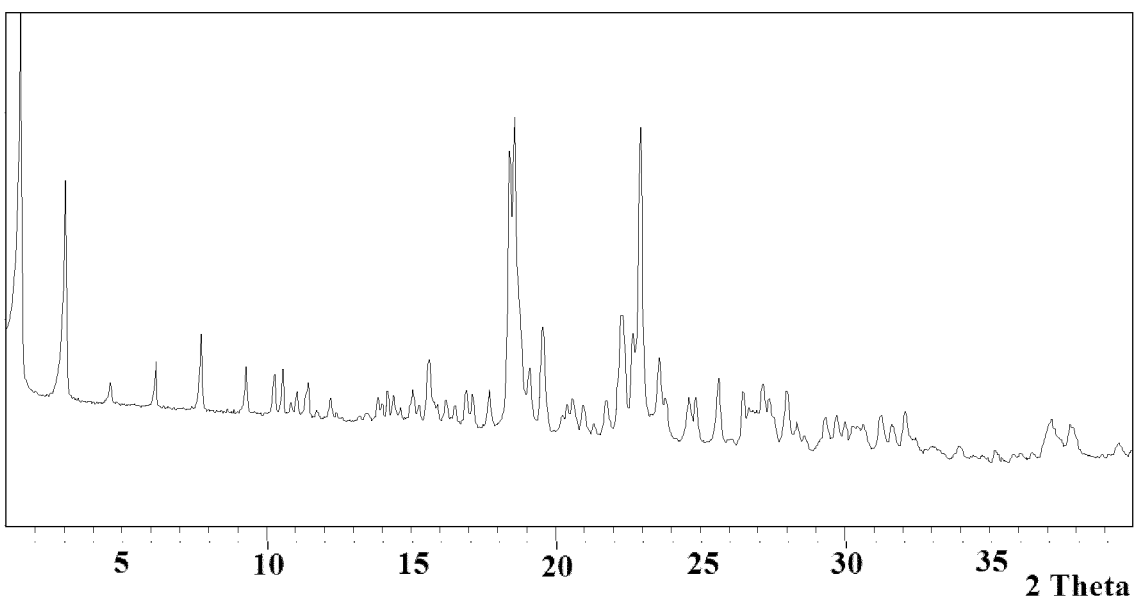
FIG. 4 shows the XRPD of cocrystal of ubiquinone and orcinol (2:3).

The cocrystal of ubiquinone and hydroquinone of the present disclosure may be further characterized by an X-ray diffractogram as in FIG. 3.

In another embodiment, the phenolic compound is hydroquinone, and the cocrystal of ubiquinone and hydroquinone is in the form of a benzyl alcohol solvate and is characterized by having an X-ray powder diffractogram that comprises characteristic peaks at approximately 1.4 and 2.9±0.3 degrees 2 theta (Cu—K$_\alpha$ radiation, λ=1.5418 Å). In still another embodiment, the cocrystal benzyl alcohol solvate of ubiquinone and hydroquinone of the present disclosure is characterized by having an X-ray powder diffractogram that further comprises characteristic peaks at 12.8, 14.3 and 22.8±0.3 degrees 2 theta (Cu—K$_\alpha$ radiation, λ=1.5418 Å).

In a particular embodiment, the molar ratio of ubiquinone, hydroquinone and benzyl alcohol is 2:1:1.

More specifically, the cocrystal of ubiquinone and hydroquinone is in the form of a benzyl alcohol solvate of the present disclosure is characterized by exhibiting in the X-ray powder diffractogram a pattern of peaks, expressed in 2 theta units in degrees, 2θ (°), which is shown in Table 3.

TABLE 3

List of selected peaks (only peaks with relative intensity greater than or equal to 1% are indicated):

| Pos. [°2Th.] | Rel. Int. [%] |
|---|---|
| 1.4033 | 3.91 |
| 2.904 | 3.03 |
| 4.3872 | 1.14 |
| 11.2788 | 8.51 |
| 11.3977 | 9.92 |
| 11.6845 | 7.68 |
| 12.1494 | 5.35 |
| 12.7662 | 3.5 |
| 13.5192 | 1.89 |
| 14.2726 | 10.36 |
| 15.051 | 2.66 |
| 18.0076 | 6.83 |
| 18.2219 | 6.19 |
| 18.5502 | 74.15 |
| 18.8826 | 63.72 |
| 19.2181 | 3.23 |
| 19.4087 | 3.42 |
| 19.5629 | 3.45 |
| 20.4535 | 2.54 |
| 21.9402 | 2.78 |
| 22.8064 | 100 |
| 23.211 | 2.24 |
| 23.6821 | 2.88 |
| 24.6521 | 3.65 |
| 29.7109 | 4.45 |
| 29.9849 | 3.21 |
| 32.1767 | 4.71 |

Figure 5:
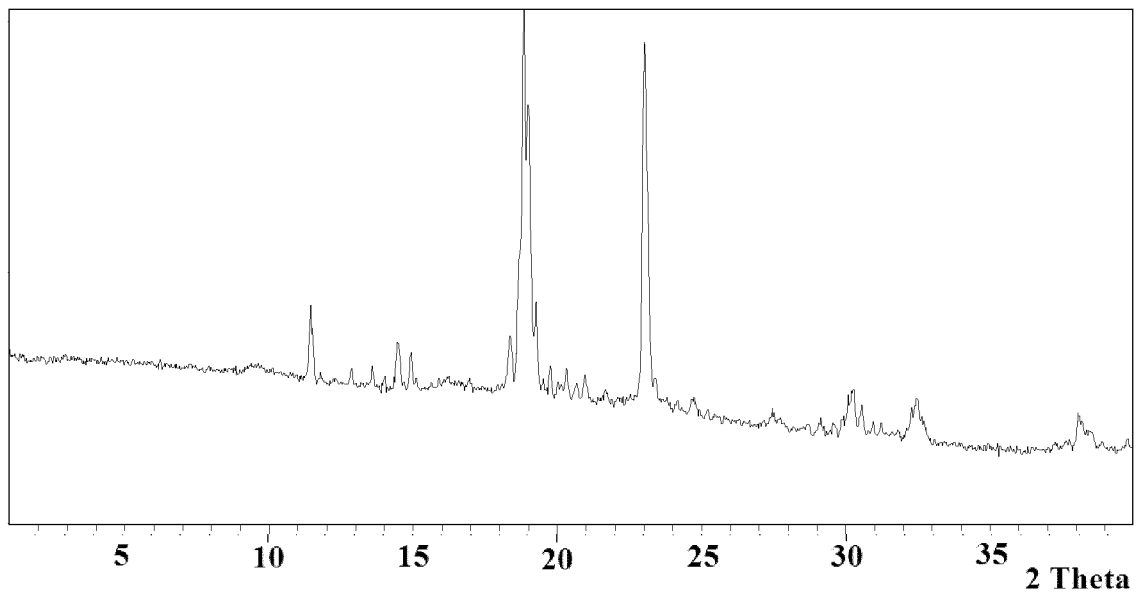
FIG. 5 shows the XRPD of cocrystal of ubiquinone and orcinol and which is in the form of a benzyl alcohol solvate (1:1:1).
Figure 6:
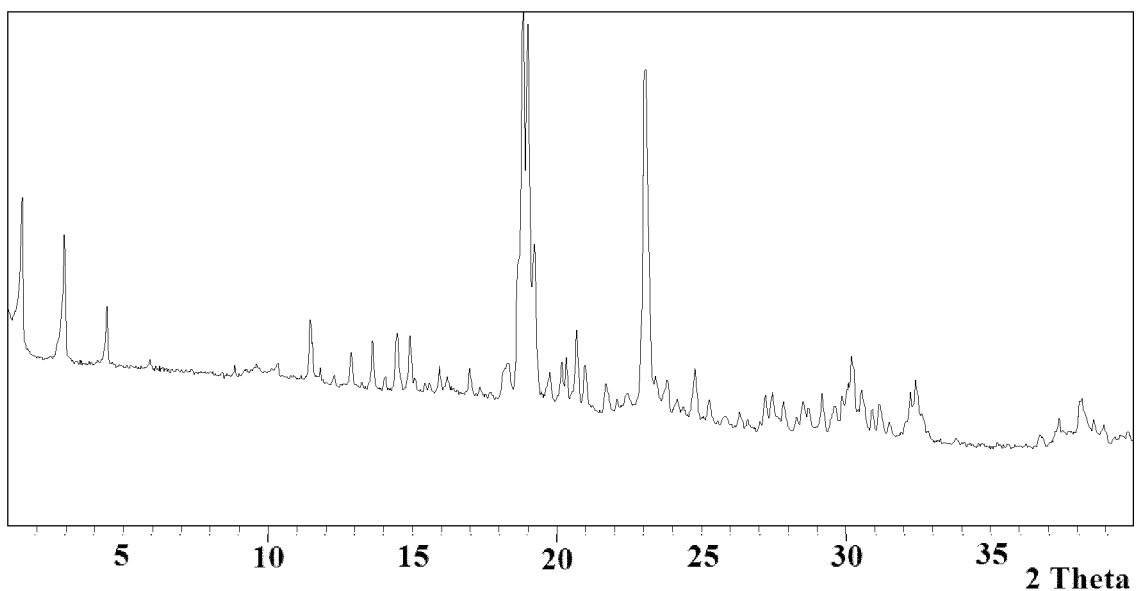
FIG. 6 shows the XRPD of cocrystal of ubiquinone and phloroglucinol in the form of a monohydrate.

The cocrystal benzyl alcohol solvate of ubiquinone and hydroquinone of the present disclosure may be further characterized by an X-ray diffractogram as in FIG. 5.

In another embodiment, the phenolic compound is orcinol and the cocrystal of ubiquinone and orcinol is characterized by having an X-ray powder diffractogram that comprises characteristic peaks at approximately 1.5 and 3.1±0.3 degrees 2 theta (Cu—K$_\alpha$ radiation, λ=1.5418 Å). In still another embodiment, the cocrystal of ubiquinone and orcinol is characterized by having an X-ray powder diffractogram that comprises further characteristic peaks at 7.8, 15.6 and 22.3±0.3 degrees 2 theta (Cu—K$_\alpha$ radiation, λ=1.5418 Å).

In a particular embodiment, the molar ratio of ubiquinone to orcinol is 2:3.

More specifically, the cocrystal of ubiquinone and orcinol of the present disclosure is characterized by exhibiting in the X-ray powder diffractogram a pattern of peaks, expressed in 2 theta units in degrees, 2θ (°), which is shown in Table 4.

TABLE 4

List of selected peaks (only peaks with relative intensity greater than or equal to 1% are indicated):

| Pos. [°2Th.] | Rel. Int. [%] |
|---|---|
| 1.5187 | 100 |
| 3.0776 | 44.01 |
| 4.6383 | 6.15 |
| 6.1968 | 8.62 |
| 7.7578 | 12.47 |
| 9.3171 | 8.01 |
| 10.2979 | 7.1 |
| 10.5835 | 7.88 |
| 11.4636 | 6.07 |
| 14.2201 | 5.27 |
| 15.1014 | 5.35 |
| 15.6357 | 8.85 |
| 16.9431 | 5.29 |
| 17.7353 | 5.35 |
| 18.4183 | 51.1 |
| 18.605 | 62.32 |
| 18.8295 | 13.97 |
| 19.1291 | 7.79 |
| 19.594 | 13.45 |
| 22.3152 | 15.12 |
| 22.6833 | 12.38 |
| 22.9486 | 59.08 |
| 23.6058 | 9.06 |
| 25.6588 | 6.64 |
| 26.4907 | 5.27 |
| 27.1826 | 5.99 |
| 28.0124 | 5.3 |

Figure 7:
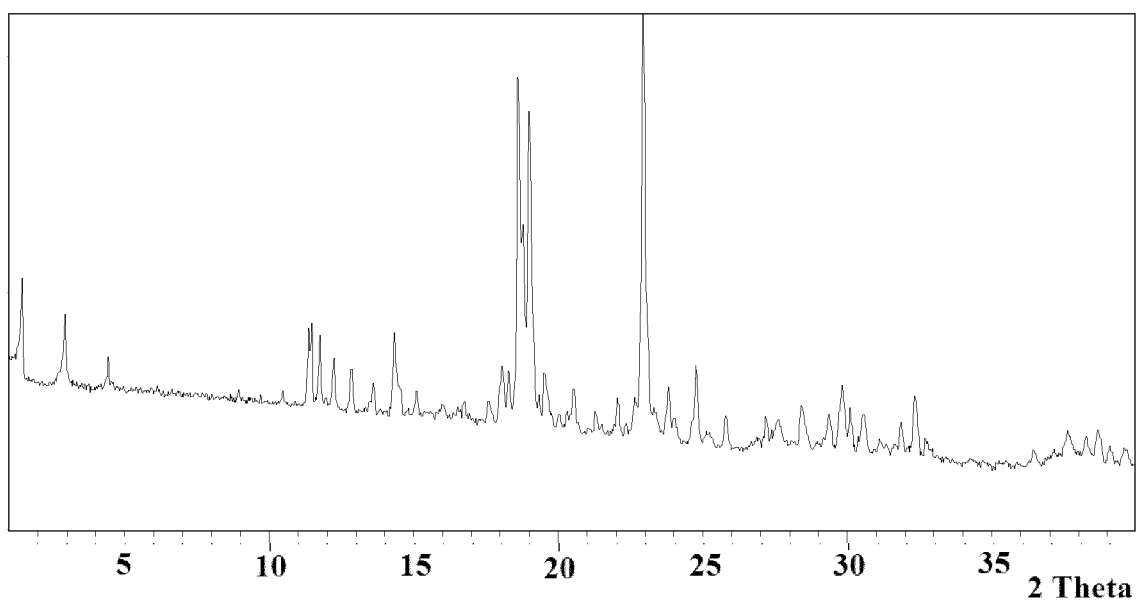
FIG. 7 shows the XRPD of cocrystal of ubiquinone and resorcinol.
Figure 8:
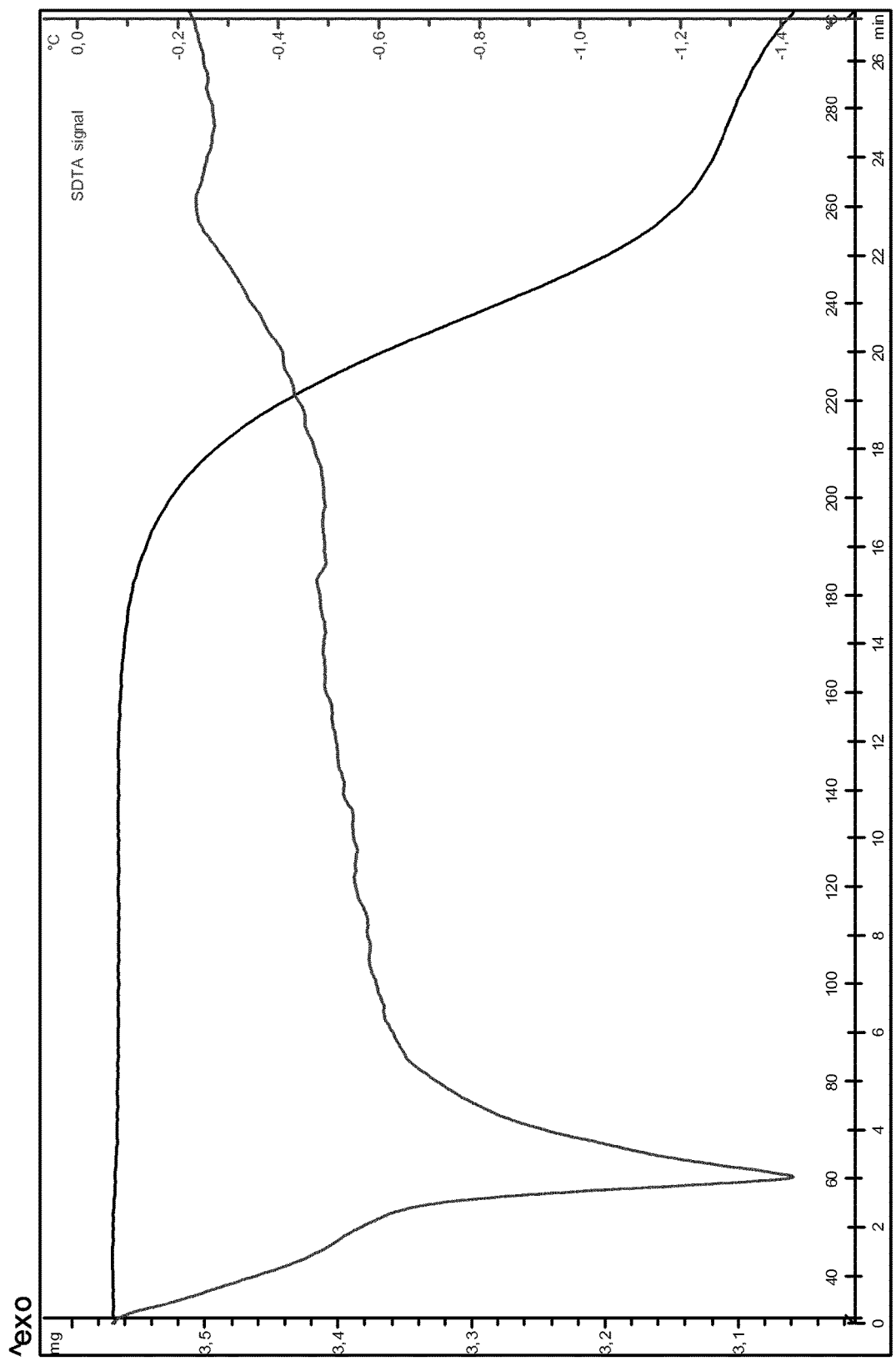
FIG. 8 shows the thermogravimetric analysis (TGA) of cocrystal of ubiquinone and 4-hydroxybenzoic acid (1:1).

The cocrystal benzyl alcohol solvate of ubiquinone and orcinol of the present disclosure may be further characterized by an X-ray diffractogram as in FIG. 7.

In another embodiment, the phenolic compound is orcinol and the cocrystal of ubiquinone and orcinol is in the form of a benzyl alcohol solvate and is characterized by having an X-ray powder diffractogram that comprises characteristic peaks at approximately 12.9 and 13.6±0.3 degrees 2 theta (Cu—K$_\alpha$ radiation, λ=1.5418 Å). In still another embodiment, the cocrystal benzyl alcohol solvate of ubiquinone and orcinol is characterized by having an X-ray powder diffractogram that comprises further characteristic peaks at 18.4, 19.0 and 23.0±0.3 degrees 2 theta (Cu—K$_\alpha$ radiation, λ=1.5418 Å).

In a particular embodiment, the molar ratio of ubiquinone, orcinol and benzyl alcohol is 1:1:1.

More specifically, the cocrystal benzyl alcohol solvate of ubiquinone and orcinol of the present disclosure is characterized by exhibiting in the X-ray powder diffractogram a pattern of peaks, expressed in 2 theta units in degrees, 2θ (°), which is shown in Table 5.

TABLE 5

List of selected peaks (only peaks with relative intensity greater than or equal to 1% are indicated):

| Pos. [°2Th.] | Rel. Int. [%] |
|---|---|
| 11.4296 | 10.7 |
| 12.8683 | 1.73 |
| 13.599 | 2.21 |
| 14.4789 | 5.55 |
| 14.922 | 4.45 |
| 16.1017 | 1.18 |
| 18.3612 | 7.84 |
| 18.8455 | 100 |
| 19.0154 | 62.19 |
| 19.2645 | 13.69 |
| 19.7626 | 4.01 |

TABLE 5-continued

List of selected peaks (only peaks with relative
intensity greater than or equal to 1% are indicated):

| Pos. [°2Th.] | Rel. Int. [%] |
|---|---|
| 20.319 | 3.82 |
| 20.6896 | 2.12 |
| 20.9558 | 3.26 |
| 21.684 | 1.83 |
| 23.0131 | 88.81 |
| 23.4127 | 3.59 |
| 24.7136 | 1.67 |
| 27.4432 | 1.2 |
| 30.078 | 3.4 |
| 30.2625 | 3.96 |
| 30.5722 | 2.52 |
| 30.9399 | 1.15 |
| 31.2389 | 1.18 |
| 32.2742 | 2.42 |
| 32.4881 | 3.58 |
| 38.0702 | 2.69 |

Figure 9:
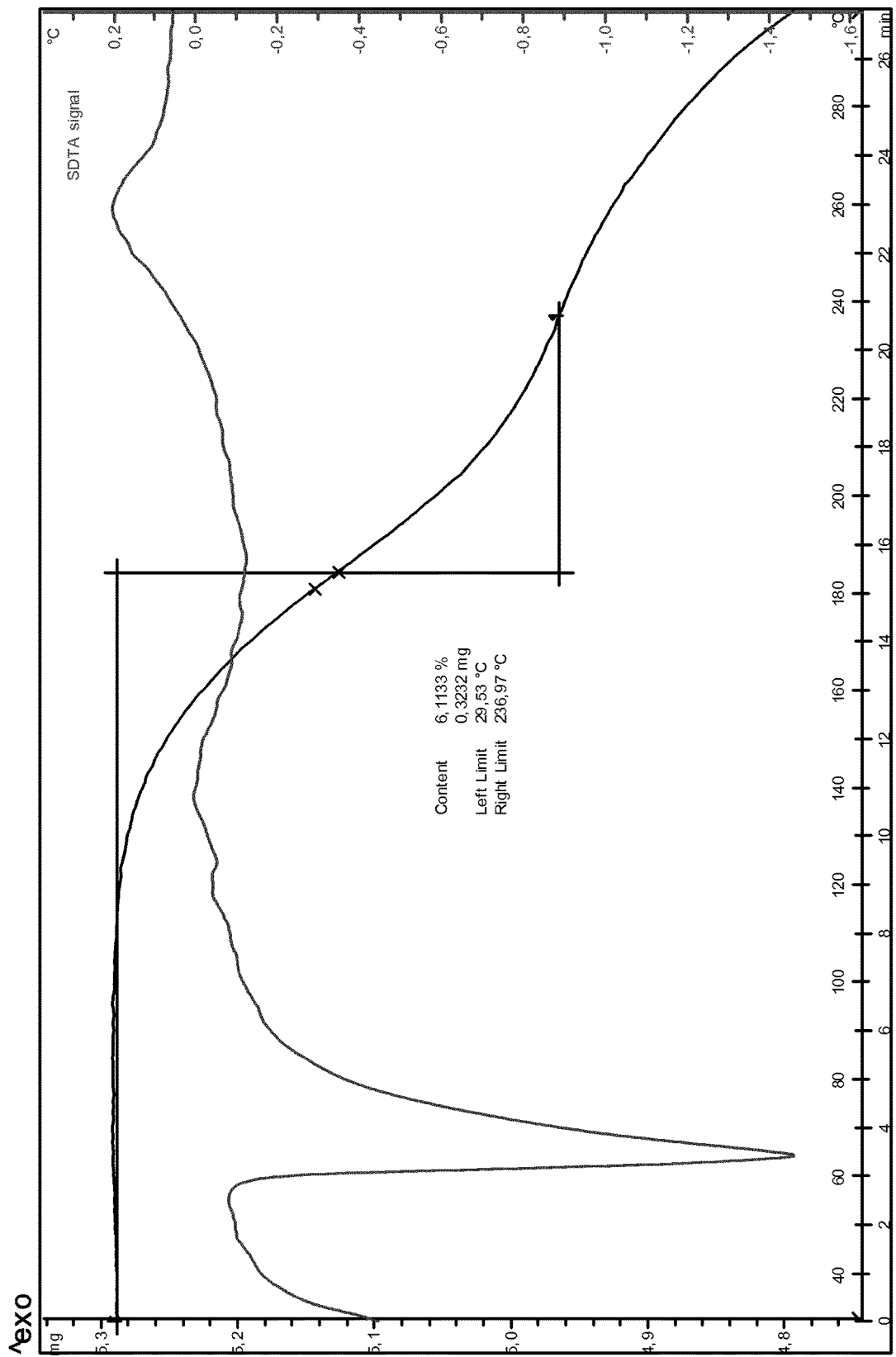
FIG. 9 shows the TGA of cocrystal of ubiquinone and hydroquinone (2:1).
Figure 10:
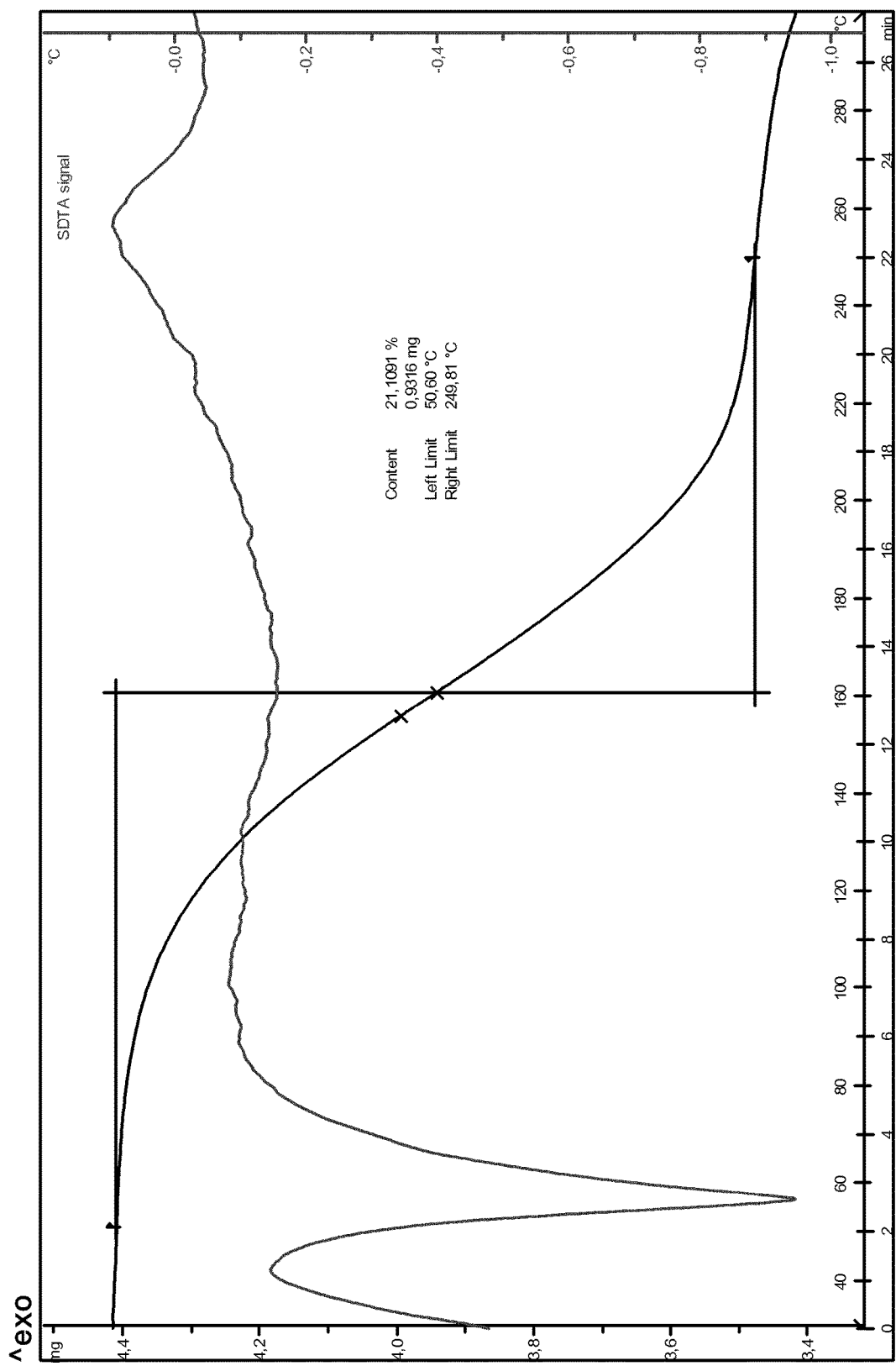
FIG. 10 shows the TGA of cocrystal of ubiquinone and hydroquinone cocrystal benzyl alcohol solvate (2:1:1).

The cocrystal benzyl alcohol solvate of ubiquinone and orcinol of the present disclosure may be further characterized by an X-ray diffractogram as in FIG. 9.

In another embodiment, the phenolic compound is phloroglucinol and the cocrystal of ubiquinone and phloroglucinol is characterized by having an X-ray powder diffractogram that comprises characteristic peaks at approximately 1.5 and 3.0±0.3 degrees 2 theta (Cu—K$_\alpha$ radiation, λ=1.5418 Å). In still another embodiment, the cocrystal of ubiquinone and phoroglucinol of the invention is characterized by having an X-ray powder diffractogram that further comprises characteristic peaks at 12.9, 13.6 and 23.0±0.3 degrees 2 theta (Cu—K$_\alpha$ radiation, λ=1.5418 Å).

In a particular embodiment, the cocrystal of ubiquinone and phloroglucinol is a monohydrate and the molar ratio of ubiquinone, phloroglucinol and water is 2:1:1.

More specifically, the cocrystal of ubiquinone and phloroglucinol of the present disclosure is characterized by exhibiting in the X-ray powder diffractogram a pattern of peaks, expressed in 2 theta units in degrees, 2θ (°), which is shown in Table 6.

TABLE 6

List of selected peaks (only peaks with relative
intensity greater than or equal to 1% are indicated):

| Pos. [°2Th.] | Rel. Int. [%] |
|---|---|
| 1.4898 | 39.45 |
| 2.9639 | 30.05 |
| 4.4374 | 16 |
| 5.9201 | 8.14 |
| 8.6606 | 7.2 |
| 9.2389 | 6.79 |
| 9.5892 | 7.58 |
| 10.3313 | 7.62 |
| 11.46 | 13.72 |
| 11.8204 | 7.08 |
| 12.8888 | 9.11 |
| 13.6313 | 10.78 |
| 14.4807 | 11.85 |
| 14.9178 | 11.39 |
| 15.9465 | 7.36 |
| 17.0027 | 7.08 |
| 18.1407 | 6.49 |
| 18.3327 | 7.66 |
| 18.6387 | 20.47 |
| 18.8401 | 100 |
| 19.0115 | 93.17 |
| 19.2305 | 27.3 |

TABLE 6-continued

List of selected peaks (only peaks with relative
intensity greater than or equal to 1% are indicated):

| Pos. [°2Th.] | Rel. Int. [%] |
|---|---|
| 20.1657 | 7.78 |
| 20.3395 | 8.28 |
| 20.6988 | 12.21 |
| 20.9757 | 7.43 |
| 23.0463 | 76.13 |
| 30.2326 | 7.97 |

Figure 11:
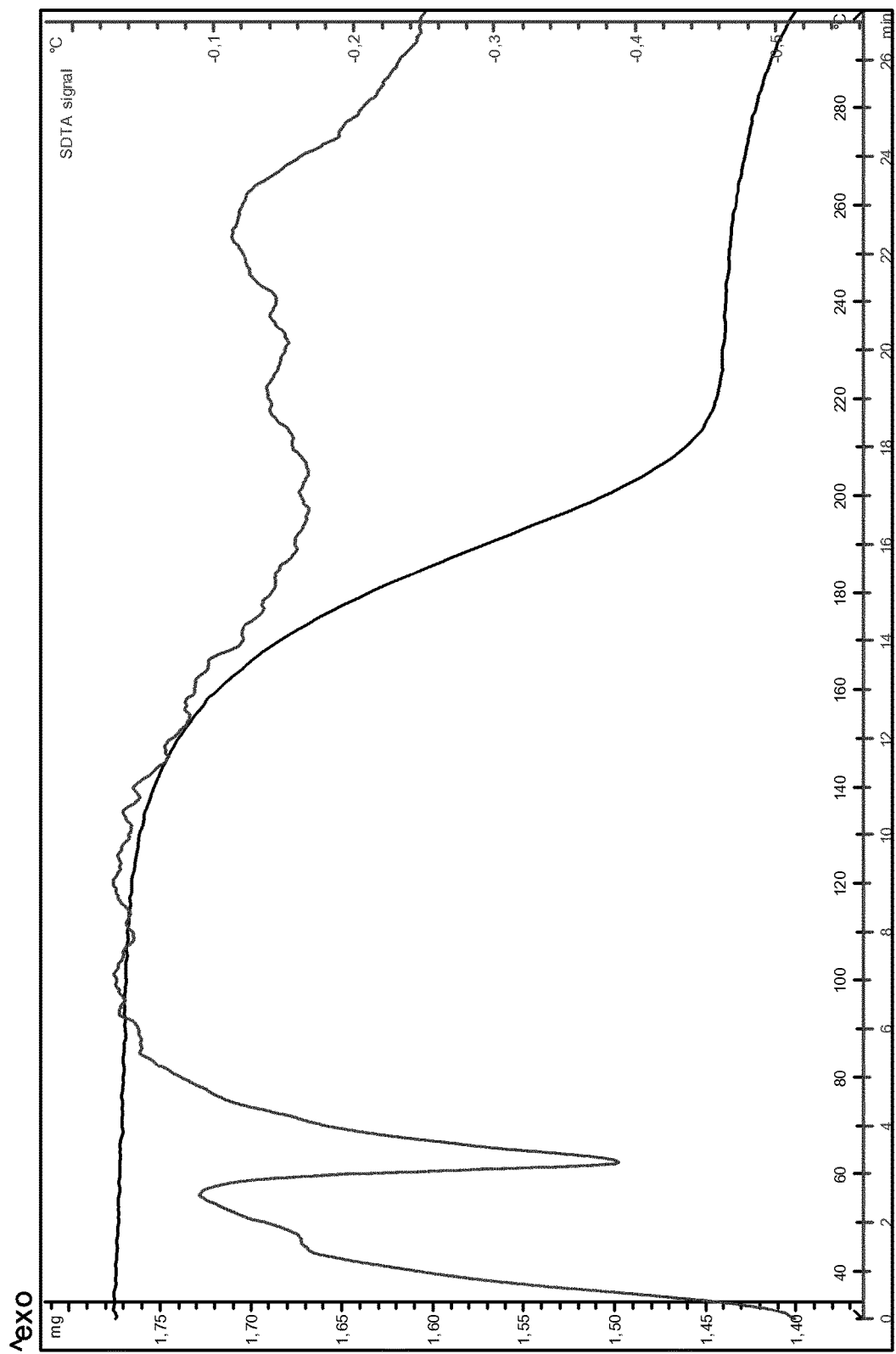
FIG. 11 shows the TGA of cocrystal of ubiquinone and orcinol (2:3).
Figure 12:
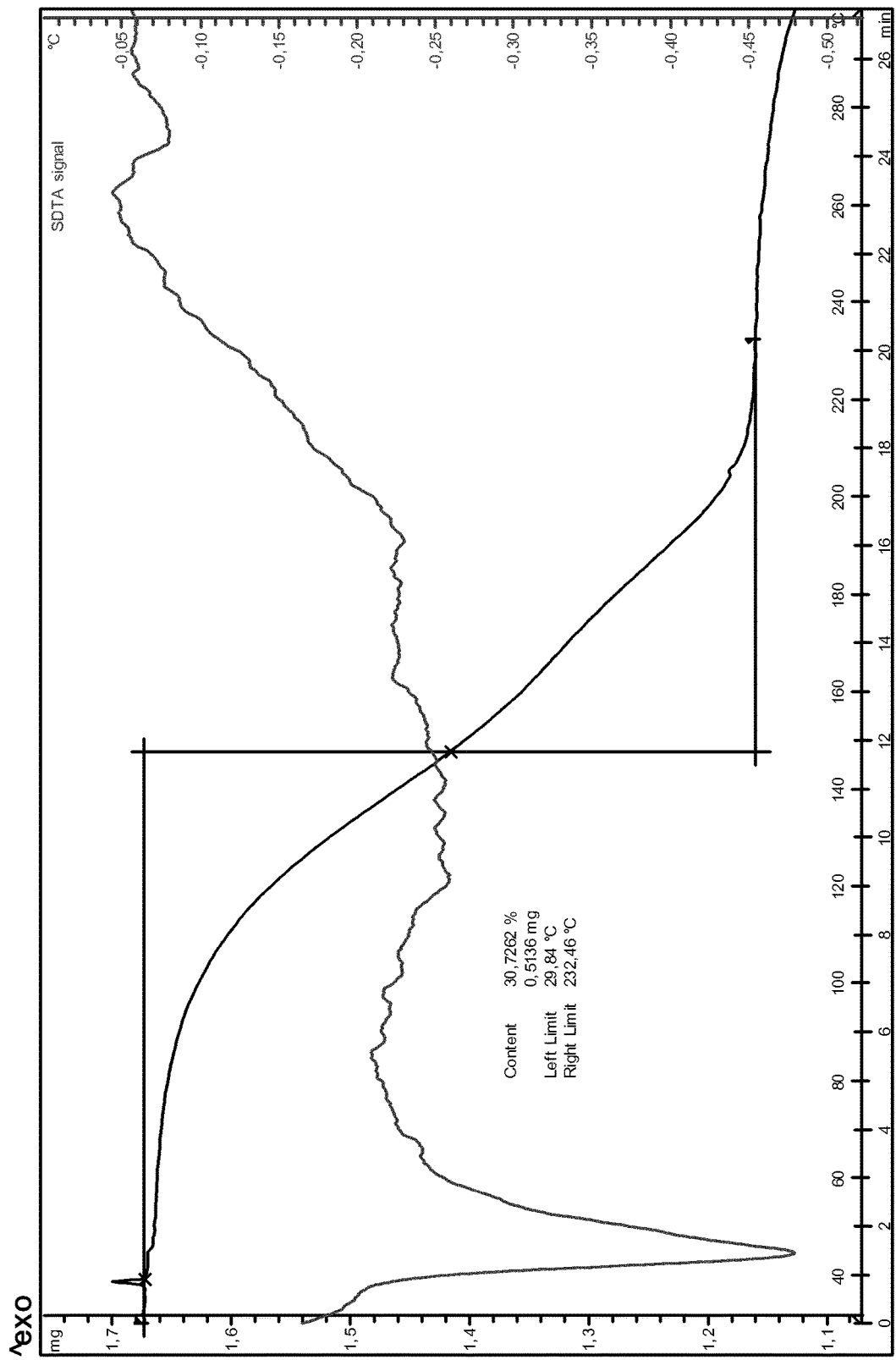
FIG. 12 shows the TGA of cocrystal of ubiquinone and orcinol and which is in the form of a benzyl alcohol solvate (1:1:1).

The cocrystal of ubiquinone and phloroglucinol of the present disclosure may be further characterized by an X-ray diffractogram as in FIG. 11.

In another embodiment, the phenolic compound is resorcinol and the cocrystal of ubiquinone and resorcinol is characterized by having an X-ray powder diffractogram that comprises characteristic peaks at approximately 1.5 and 3.0±0.3 degrees 2 theta (Cu—K$_\alpha$ radiation, λ=1.5418 Å). In still another embodiment, the cocrystal of ubiquinone and resorcinol is characterized by having an X-ray powder diffractogram that further comprises characteristic peaks at 12.9, 13.6 and 22.9±0.3 degrees 2 theta (Cu—K$_\alpha$ radiation, λ=1.5418 Å).

In a particular embodiment, the molar ratio of ubiquinone to resorcinol is 2:1.

More specifically, the cocrystal of ubiquinone and resorcinol of the present disclosure is characterized by exhibiting in the X-ray powder diffractogram a pattern of peaks, expressed in 2 theta units in degrees, 2θ (°), which is shown in Table 7.

TABLE 7

List of selected peaks (only peaks with relative
intensity greater than or equal to 1% are indicated):

| Pos. [°2Th.] | Rel. Int. [%] |
|---|---|
| 1.4518 | 16.92 |
| 2.9485 | 9.47 |
| 10.4657 | 1.32 |
| 11.3574 | 9.44 |
| 11.4822 | 10.27 |
| 11.7679 | 9.03 |
| 12.2347 | 5.8 |
| 12.8524 | 4.44 |
| 13.6231 | 2.9 |
| 14.3461 | 9.68 |
| 15.1261 | 2.41 |
| 18.0735 | 5.86 |
| 18.2936 | 5.38 |
| 18.6274 | 77.96 |
| 19.0096 | 63.49 |
| 19.5462 | 5.36 |
| 20.5573 | 3.85 |
| 22.0579 | 3.11 |
| 22.6484 | 3.36 |
| 22.9362 | 100 |
| 23.8212 | 4.7 |
| 24.7869 | 7.39 |
| 28.4279 | 3.59 |
| 29.8287 | 5.79 |
| 30.1043 | 3.7 |
| 30.5748 | 2.98 |
| 31.8529 | 2.47 |
| 32.3288 | 4.66 |

Figure 13:
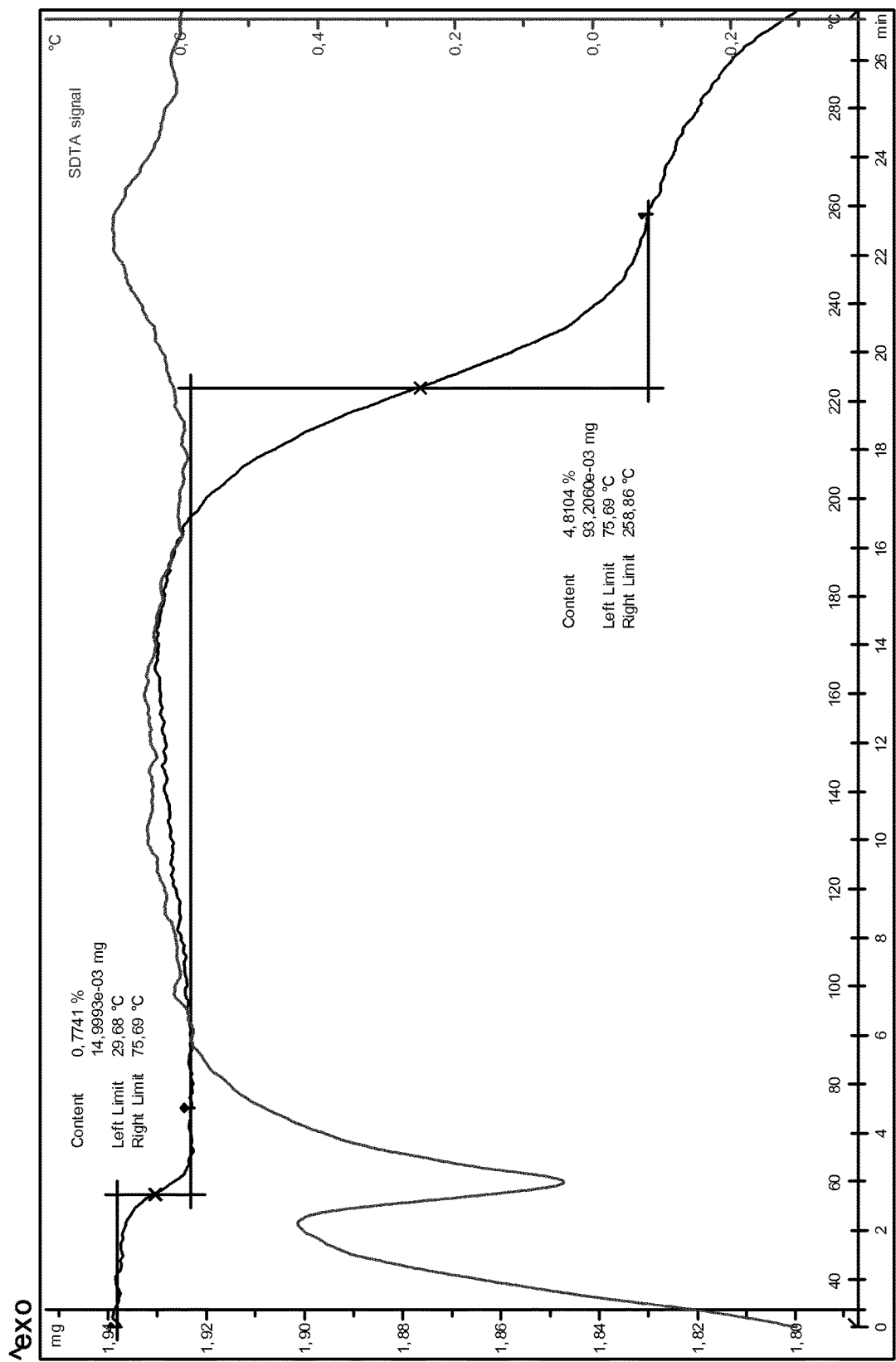
FIG. 13 shows the TGA of cocrystal of ubiquinone and phloroglucinol in the form of a monohydrate.
Figure 14:
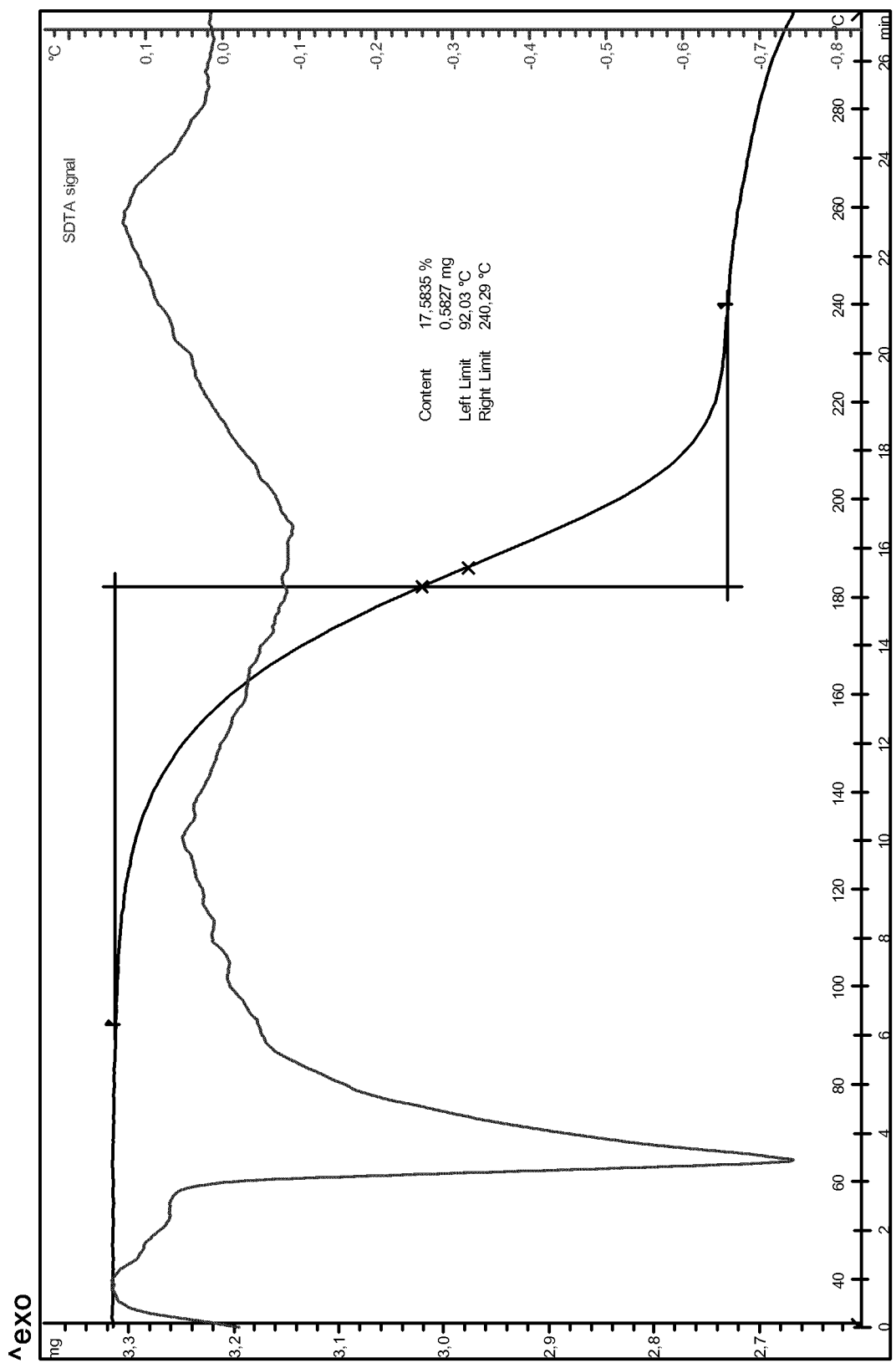
FIG. 14 shows the TGA of cocrystal of ubiquinone and resorcinol.

The cocrystal of ubiquinone and resorcinol of the present disclosure may be further characterized by an X-ray diffractogram as in FIG. 13.

In another embodiment, the phenolic compound is 2,4-dihydroxybenzoic acid and the cocrystal of ubiquinone and 2,4-dihydroxybenzoic acid of the present invention is characterized by having an X-ray powder diffractogram that comprises characteristic peaks at approximately 1.4 and 18.7±0.3 degrees 2 theta (Cu—K$_\alpha$ radiation, λ=1.5418 Å). In still another embodiment, the cocrystal of ubiquinone and 2,4-dihydroxybenzoic acid of the invention is characterized by having an X-ray powder diffractogram that comprises further characteristic peaks at 2.8, 4.2, 19.3 and 22.8±0.3 degrees 2 theta (Cu—K$_\alpha$ radiation, λ=1.5418 Å).

More specifically, the cocrystal of ubiquinone and 2,4-dihydroxybenzoic acid of the present disclosure is characterized by exhibiting in the X-ray powder diffractogram a pattern of peaks, expressed in 2 theta units in degrees, 2θ (°), which is shown in Table 8.

TABLE 8

List of selected peaks (only peaks with relative intensity greater than or equal to 1% are indicated):

| Pos. [°2Th.] | Rel. Int. [%] |
| --- | --- |
| 1.3891 | 97.92 |
| 2.8012 | 51.11 |
| 4.208 | 13.21 |
| 12.8877 | 6.61 |
| 18.7289 | 92.6 |
| 18.8854 | 70.67 |
| 19.2786 | 19.4 |
| 22.8335 | 100 |

It is also part of the invention the provision of a process for the preparation of the cocrystal of ubiquinone and a hydrogen bond donor coformer, said process comprising the steps of:
a) either preparing a concentrated solution of the hydrogen bond donor coformer in an organic solvent selected from the list consisting of methanol, ethanol, isopropanol, butanol, methyl ethyl ketone, acetone, methyl isobutyl ketone, dimethylformamide, pentane, heptane, cyclohexane, toluene, xylene, ethyl acetate, diethyl ether, tetrahydrofuran, ethylene glycol dimethyl ether, diisopropyl ether, dioxane, dichloromethane, chloroform, acetic acid, benzyl alcohol, formic acid, dimethyl sulfoxide, ethylene glycol, water, aqueous ammonia, diethylamine, and mixtures thereof; and adding ubiquinone until a suspension is observed;
or, alternatively, preparing a suspension of ubiquinone and the hydrogen bond donor coformer in the organic solvent;
b) stirring the suspension at room temperature until the cocrystal is formed; and
c) isolating the cocrystal thus obtained.

In an embodiment, step a) is carried out at room temperature.

In another embodiment, optionally in combination with one or more features of the particular embodiments of the process defined above, the isolation step c) may include removing the organic solvent, for example, by one or more of the following operations: filtration, filtration under vacuum, decantation, and centrifugation, or other suitable techniques as known to a person skilled in the art. Particularly, step c) is carried out by filtration of the solid. In another embodiment, step c) further comprises drying the isolated cocrystal. Particularly, the cocrystal is dried at room temperature, more particularly under vacuum conditions. Generally, the vacuum involves a pressure from 0.5 mbar to 3 mbar.

Particularly, the hydrogen bond donor coformer is a phenolic compound such as 4-hydroxybenzoic acid, hydroquinone, orcinol, phloroglucinol, resorcinol, and 2,4-dihydroxybenzoic acid. Ubiquinone, and the coformers, particularly the phenolic compounds mentioned above, used as starting materials in the present invention are commercially available.

As an example, the cocrystal of ubiquinone and the phenolic compound may be obtained by:
a) preparing a concentrated solution of the phenolic compound, such as hydroquinone, orcinol, or 2,4-dihydroxybenzoic acid, in the organic solvent as defined above and adding ubiquinone until a suspension is observed;
b) stirring the suspension at room temperature; and
c) filtering and drying the solid obtained.

In a particular embodiment, the phenolic compound is hydroquinone and the organic solvent is benzyl alcohol.

In a particular embodiment, the phenolic compound is orcinol and the organic solvent is benzyl alcohol.

Alternatively, the cocrystal of ubiquinone and the phenolic compound may be obtained by:
a) preparing a suspension of ubiquinone and the phenolic compound coformer, such as 4-hydroxybenzoic acid, hydroquinone, orcinol, phloroglucinol or resorcinol in the organic solvent;
b) stirring the suspension at room temperature; and
c) filtering and drying the solid obtained.

In a particular embodiment, the phenolic compound is 4-hydroxybenzoic acid and the organic solvent is ethyl acetate.

In a particular embodiment, the phenolic compound is hydroquinone and the organic solvent is acetic acid.

In a particular embodiment, the phenolic compound is orcinol and the organic solvent is heptane.

In a particular embodiment, the phenolic compound is resorcinol and the organic solvent is heptane.

In a particular embodiment, the phenolic compound is phloroglucinol and the organic solvent is benzyl alcohol.

In a particular embodiment, the phenolic compound is of 2,4-dihydroxybenzoic acid and the organic solvent is acetone.

Particularly, in any one of the processes above the stirring is carried out for 10 to 72 hours.

The compounds of the present disclosure are characterized by having a particle size of the same order of magnitude as that of commercialized ubiquinone. Thus, their higher dissolution rate with respect to ubiquinone is an intrinsic feature of the compounds of the invention and is not due to an effect of the particle size.

In a particular embodiment, optionally in combination with one or more features of the particular embodiments of the process defined above, the compounds of the present disclosure have a particle size distribution wherein $D_{90}$ is equal to or lower than 45 μm, particularly from 30 μm to 40 μm.

In another embodiment, optionally in combination with one or more features of the particular embodiments of the process defined above, the compounds of the present disclosure have a particle size distribution wherein $D_{50}$ is equal to or lower than 30 μm, particularly from 10 μm to 25 μm.

In still another embodiment, optionally in combination with one or more features of the particular embodiments of the process defined above, the compounds of the present disclosure have a particle size distribution wherein $D_{10}$ is equal to or lower than 10 μm.

The cocrystals of ubiquinone and a hydrogen bond donor coformer as defined above the invention may also be defined by its preparation process. Accordingly, this aspect of the invention can be formulated as the cocrystals of ubiquinone and a hydrogen bond donor coformer as defined above obtainable by the previous process, optionally including any preferred or particular embodiment of the processes and possible combinations of some of the process features disclosed above.

The second aspect of the invention relates to a composition comprising an effective amount of a cocrystal of ubiquinone and a hydrogen bond donor coformer as defined above together with one or more appropriate acceptable excipients or carriers.

The term "effective amount" refers to the amount of the cocrystal which provides a therapeutic effect after its application.

In an embodiment, the composition of the second aspect of the invention is a pharmaceutical composition comprising a pharmaceutically effective amount of a cocrystal of ubiquinone and a hydrogen bond donor coformer as defined above together with one or more appropriate pharmaceutically acceptable excipients or carriers. The term "pharmaceutical composition" refers to a mixture of a cocrystal disclosed herein with other chemical components, such as diluents or carriers. The pharmaceutical composition facilitates administration of the cocrystal to an organism. Particularly, the pharmaceutical composition can be formulated for inhaled, intramuscular, subcutaneous, oral, or topical, administration.

In an embodiment, the composition of the second aspect of the invention is a dietary supplement comprising an effective amount of a cocrystal of ubiquinone and a hydrogen bond donor coformer as defined above together with one or more appropriate orally acceptable excipients or carriers. The term "dietary supplement" refers to a product taken orally that contains an ingredient intended to supplement the diet. Dietary supplements can be in form of tablets, capsules, softgels, gelcaps, liquids, powders, bars, drinks, shakes and other food products. As an example, the dietary supplement may be to enhance athletic performance.

The terms "acceptable excipients or carriers" refers to acceptable material, composition or vehicle, such as liquid or solid filler, diluent, excipient, solvent, or encapsulating material. Each component must be acceptable in the sense of being compatible with the other ingredients of the composition. It must also be suitable for use in contact with the tissue or organ of humans and animals without excessive toxicity, irritation, allergic response, immunogenicity or other problems or complications commensurate with a reasonable benefit/risk ratio. In pharmaceutical compostions the acceptable excipient or carrier is a pharmaceutically acceptable excipient or carrier.

In a particular embodiment, the pharmaceutical composition as defined above further comprises one or more active ingredients selected from the group consisting of cardiovascular agents, antilipemic agents, antidiabetic agents, and antiplatelet agents. In a particular embodiment, the dietary supplement as defined above further comprises one or more active ingredients selected from the group consisting of L-carnitine, xylitol, vitamins, carotenoids, flavonoids, copper, zinc, and manganese.

Examples of cardiovascular agents include, but would not be limited to, alpha andrenergic agonists such as adrafinil, adrenalone, amidephrine, apraclonidine, budralazine, clonidine, cyclopentamine, dexmedetomidine, dimetofrine, dipivefrin, ecabapide, ephedrine, epinephrine, fenoxazoline, guanabenz, guanfacine, hydroxyamphetamine, ibopamine, indanazoline, isometheptene, mephentermine, metaraminol, methoxamine, methylhexaneamine, midodrine, mivazerol, modafinil, moxonidine, naphazoline, norepinephrine, norfenefrine, octodrine, octopamine, oxymetazoline, phenylephrine, hydrochloride, phenylpropanolamine, phenylpropyl methylamine, pholedrine, propylhexedrine, pseudoephedrine, rilmenidine, synephrine, talipexole, tetrahydrozoline, tiamenidine, tramazoline, tuaminoheptane, tymazoline, tyramine, and xylometazoline; beta andrenergic agonists such as albuterol, bambuterol, bitolterol, carbuterol, clenbuterol, clorprenaline, denopamine, dixoethedrine, dopexamine, ephedrine, epinephrine, etafedrine, ethylnorepinephrine, fenoterol, formoterol, hexoprenaline, Ibopamine, isoetharine, isoproterenol, methoxyphenamine, mabuterol, metaproterenol, oxyfedrine, pirbuterol, prenalterol, procaterol, protokylol, reproterol, rimiterol, ritodrine, salmeterol, soterenol, terbutaline, tretoquinol, tulobuterol, and xamoterol; alpha andrenergic blockers such as amosulalol, arotinolol, dapiprazole, doxazosin, ergoloid mesylates, fenspiride, Idazoxan, Indoramin, labetalol, monatepil, naftopidil, nicergoline, prazosin, tamsulosin, terazosin, tolazoline, trimazosin and yohimbine; beta andrenergic blockers such as acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, butidrine hydrochloride, butofilol, carazolol, carteolol, carvedilol, celiprolol, cetamolol, cloranolol, dilevalol, esmolol, Indenolol, labetalol, landiolol, levobunolol, mepindolol, metipranolol, metoprolol, moprolol, nadolol, nadoxolol, nebivolol, nifenalol, nipradilol, oxprenolol, penbutolol, pindolol, practolol, pronethalol, propanolol, sotalol, sulfinalol, talinolol, tertatolol, tilisolol, timolol, toliprolol and xibenolol; antiarrhythmics such as acebutolol, acecainide, adenosine, ajmaline, alprenolol, amiodarone, aprindine, arotinolol, atenolol, azimilide, bevantolol, bidisomide, bretylium tosylate, bucumolol, bufetolol, bunaftine, bunitrolol, bupranolol, butidrine hydrochloride, butobendine, capobenic acid, carazolol, carteolol, cifenline, cloranolol, disopyramide, dofetilide, encainide, esmolol, flecainide, hydroquinidine, Ibutilide, Indecainide, Indenolol, ipratropium bromide, landiolol, lidocaine, lorajmine, lorcainide, meobentine, mexiletine, moricizine, nadoxolol, nifenalol, oxprenolol, penbutolol, pentisomide, pilsicainide, pindolol, pirmenol, practolol, prajmaline, procainamide hydrochloride, pronethalol, propafenone, propranolol, pyrinoline, quinidine, sematilide, sotalol, talinolol, tedisamil, tilisolol, timolol, tocainide, verapamil and xibenolol; calcium channel blockers such as arylalkylamines: bepridil, clentiazem, diltiazem, fendiline, gallopamil, mibefradil, prenylamine, semotiadil, terodiline, verapamil; dihydropyridine derivatives such as amlodipine, aranidipine, bamidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, piperazine derivatives such as cinnarizine, dotarizine, flunarizine, lidoflazine, lomerizine; and others such as bencyclane, etafenone, fantofarone, monatepil, and perhexiline; vasodilators such as amotriphene, benfurodil hemisuccinate, benziodarone, chloracizine, chromonar, clobenfurol, clonitrate, cloricromen, dilazep, droprenilamine, efloxate, erythrityl tetranitrate, etafenone, fendiline, hexestrol bis ([β-diethylaminoethyl) ether, hexobendine, Itramin tosylate, khellin, lidoflazine, mannitol hexanitrate, nitroglycerin, pentaerythritol tetranitrate, pentrinitrol, perhexiline, pimefylline, prenylamine, propatyl nitrate, trapidil, tricromyl, trimetazidine, trolnitrate phosphate and visnadine; vasopressors such as antihypotensive: amezinium methyl sulfate, angiotensin amide, dopamine, dimetofrine, etifelmin, etilefrin, gepefrine, metaraminol, methoxamine, midodrine, norepinephrine, pholedrine and synephrine; and inotropic agents such as digoxin, milrinone, dobutamine, and dopamine.

Examples of antilipemic agents include, but would not be limited to, bile acid sequesterants such as cholestyramine resin, cholesevelam hydrochloride, colestipol, and polidexide; fibric acid derivatives such as bezafibrate, binifibrate, ciprofibrate, clinofibrate, clofibrate, clofibric acid, etofibrate, fenofibrate, gemfibrozil, pirifibrate, ronifibrate, simfibrate and theofibrate; hmg coa reductase inhibitors such as atorvastatin, cerivastatin, fluvastatin, lovastatin, pravastatin sodium, pitavastatin, rosuvastatin and simvastatin; omega-3-fatty acids such as eicosapentaenoic acid, docosahexaenoic acid, and docosapentaenoic acid; and nicotidine acid derivatives such as acipimox, aluminum nicotinate, niceritrol, nicoclonate, nicomol, and oxiniacic acid; and other antilipemic agents such as acifran, benfluorex, β-benzalbutyramide, carnitine, chonodroitin sulfate, clomestrone, detaxtran, dextran sulfate sodium, eicosapentaenoic acid, eritadenine, ezetimibe, furazabol, meglutol, melinamide, υ-oryzanol, pantethine, pentaerythritol tetraacetate, α-phenylbutyramide, pirozadil, probucol, resveratrol, β-sitosterol, sultosilic acid, tiadenol, triparanol, and xenbucin.

Examples of antidiabetic agents include, but would not belimited to, biguanides (i.e., metformin, buformin, phenformin), sulfonylureas (i.e., acetohexamide, carbutamide, chlorpropamide, glibomuride, gliclazide, glimepiride, glipizide, gliquidone, glisoxepid, glyburide, glybuthiazole, glybuzole, glyhexamide, glymidine, glypinamide, phenbutamide, tolazamide, tolbutamide, tolcyclomide), thiazolidinediones (i.e., piogliatazone, rosiglitazone, troglitazone), beta andrenergic blockers, and other antidiabetics such as acarbose, calcium mesoxalate, miglitol, nateglinide, repaglinide, voglibose.

Examples of antiplatelet agents include, but would not limited to, tirofiban, dipyridamole, anagrelide, epoprostanol, eptifibatide, clopidrogel, cilostazole and triclopidine.

Examples of vitamins include but are not limited to Vitamin A (acetate or palmitate, betacarotene), vitamin B1 (thiamine (aneurine)) (hydrochloride or mononitrate), B2 (riboflavin), vitamin B6 (pyridoxine hydrochloride), vitamin B12 (cobalamin), vitamin B12 (cyanocobalamin), vitamin B12 (mecobalamin), vitamin C (ascorbic acid), nicotinic acid, vitamin D2 (ergo-calciferol), vitamin D3 (cholecalciferol), vitamin E (alpha tocopheryl acetate, alpha tocopheryl succinate, alpha tocopherol, γ-tocopherol), vitamin K (phylloquinone, menadione etc), and nicotinamide riboside.

Examples of carotenoids include, but are not limited to, lutein, lycopene, α-carotene, β-carotene, γ-carotene, β-cryptoxanthin, Capsanthin, Zeaxanthin, Astaxanthin.

Examples of flavonoids include, but are not limited to, kaempferol, myricetin, quercetin, rutin, catechin, epicatechin, ECG, gallocatechin, EGC, EGCG, cyanidin, caffeic acid, theaflavin, theaflavin gallate, luteolin, daidzein, genestein, and glycitein.

The compositions of the present invention can be prepared according to methods well known in the state of the art. The appropriate excipients and/or carriers, and their amounts, can readily be determined by those skilled in the art according to the type of formulation being prepared.

All the embodiments disclosed above for the cocrystals of ubiquinone as defined above also applies to the compositions of the invention.

The third aspect of the invention relates to a cocrystal of ubiquinone and a hydrogen bond donor coformer as defined above for use as a medicament.

Particularly, the cocrystal of ubiquinone and a hydrogen bond donor coformer as defined above is for use in the prophylaxis and/or treatment of CoQ10 deficiencies, gingivitis, heart failure, angina, mitochondrial disorders, fibromyalgia, cardiovascular disease, atherosclerosis, dyslipidemia, hypertension, diabetes, cancer, infertility, and neurodegenerative diseases such as Parkinson's disease, Huntington's disease, Alzheimer's disease, and Friedreich's ataxia. This aspect could be also formulated as the use of the a cocrystals of ubiquinone and a hydrogen bond donor coformer, such as a benzoic acid as defined above, for the preparation of a medicament for the prophylaxis and/or treatment of CoQ10 deficiencies, gingivitis, heart failure, angina, mitochondrial disorders, fibromyalgia, cardiovascular disease, atherosclerosis, dyslipidemia, hypertension, diabetes, cancer, infertility, and neurodegenerative diseases such as Parkinson's disease, Huntington's disease, Alzheimer's disease, and Friedreich's ataxia. It also relates to a method for the prophylaxis and/or treatment of a mammal suffering, or susceptible to suffer, from CoQ10 deficiencies, gingivitis, heart failure, angina, mitochondrial disorders, fibromyalgia, cardiovascular disease, atherosclerosis, dyslipidemia, hypertension, diabetes, cancer, infertility, and neurodegenerative diseases such as Parkinson's disease, Huntington's disease, Alzheimer's disease, and Friedreich's ataxia, wherein the method comprises administering to said mammal an effective amount of the cocrystal of ubiquinone and a hydrogen bond donor coformer as defined above, together with one or more acceptable excipients or carriers.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

General Considerations

Ubiquinone, 4-hydroxybenzoic acid, hydroquinone, orcinol, phloroglucinol, resorcinol, and 2,4-dihydroxybenzoic acid are commercially available.

Powder X-Ray diffraction (PXRD) analyses were performed by sandwiching the powder samples between polyester films of 3.6 microns of thickness analysed in a PANalytical X'Pert PRO MPD θ/θ powder diffractometer of 240 millimetres of radius, in a configuration of convergent beam with a focalizing mirror and a flat sample transmission geometry, in the following experimental conditions: Cu Kα radiation ($\lambda=1.5418$ Å); Work power: 45 kV and 40 mA; Incident beam slits defining a beam height of 0.4 millimetres; Incident and diffracted beam 0.02 radians Soller slits;

PIXcel detector: Active length=3.347°; 2θ/θ scans from 2 to 40° 2θ with a step size of 0.026° 2θ and a measuring time of 76 seconds per step.

Thermogravimetric analysis (TGA) was performed on a Mettler-Toledo TGA-851e thermobalance. Experimental conditions: alumina crucibles of 70 µL volume, atmosphere of dry nitrogen with 50 mL/min flow rate, heating rate of 10° C./min.

Example 1.—Preparation of a Cocrystal of Ubiquinone:4-Hydroxybenzoic Acid (1:1)

Ubiquinone (474 mg, 0.549 mol) and 4-hydroxybenzoic acid (69 mg, 0.500 mol) were suspended in AcOEt (0.6 mL) at room temperature for 3 days. A compact solid was formed and it was filtered and dried under vacuum.

Example 2.—Preparation of a Cocrystal of Ubiquinone:Hydroquinone (2:1)

Ubiquinone (443.4 mg, 0.514 mol) and hydroquinone (67.9 mg, 0.617 mol) were suspended in acetic acid (2.0 mL) at room temperature overnight. The suspension was transferred into a flask and it was washed with 4.0 mL of acetic acid. The new suspension was stirred at room temperature for 3 days. The resulting solid was filtered and dried under vacuum.

Example 3.—Preparation of a Cocrystal of Ubiquinone:Hydroquinone Cocrystal Benzyl Alcohol Solvate (2:1:1)

A saturated solution of hydroquinone (100 mg) in benzyl alcohol (1 mL) was prepared by heating a hydroquinone/benzyl alcohol suspension up to 65° C. until total dissolution and subsequently let to cool down at room temperature. Then, ubiquinone (45 mg) was added until a suspension was formed. The suspension was stirred at room temperature overnight. The solid was filtered and dried under vacuum.

Example 4.—Preparation of a Cocrystal of Ubiquinone:Orcinol (2:3)

Ubiquinone (489.8 mg, 0.567 mol) and orcinol (33.5 mg, 0.270 mol) were suspended in heptane (2.0 mL) at room temperature and stirred overnight. The resulting solid was filtered and dried under vacuum.

Example 5.—Preparation of a Cocrystal of Ubiquinone:Orcinol Cocrystal Benzyl Alcohol Solvate (1:1:1)

A saturated solution of orcinol (100 mg) in benzyl alcohol (0.25 mL) was prepared at room temperature. Then, ubiquinone (41 mg) was added until a suspension was formed. The suspension was stirred at room temperature overnight. The solid was filtered and dried under vacuum.

Example 6.—Preparation of a Cocrystal of Ubiquinone:Phloroglucinol Monohydrate Cocrystal (2:1:1)

Ubiquinone (512.6 mg, 0.594 mol) and phloroglucinol (34 mg, 0.270 mol) were suspended in DIE (2.0 mL) at room temperature and stirred for 3 days. The solid was filtered and dried under vacuum.

Example 7.—Preparation of a Cocrystal of Ubiquinone:Resorcinol Cocrystal (2:1)

Ubiquinone (493.5 mg, 0.572 mol) and resorcinol (30.0 mg, 0.272 mol) were suspended in heptane (3.0 mL) at room temperature and stirred overnight. The suspension was transferred into a flask and it was washed with 2.0 mL of heptane. The new suspension was stirred at room temperature for 3 days. The solid was filtered and dried under vacuum.

Example 7.—Preparation of a Cocrystal of Ubiquinone:2,4-Dihydroxybenzoic Acid A saturated solution of 2,4-dihydroxybenzoic acid (100 mg) in acetone (0.15 mL) was prepared at room temperature. Then, ubiquinone (56 mg) was added until a suspension was formed. The suspension was stirred at room temperature overnight. The solid was filtered and dried under vacuum.

Example 9.—Particle Size Analysis

Nomenclature

Average of the sphere equivalent volume: Mean, D(4,3)
Sauter medium diameter: D(3,2)
Cumulative volume at 10%: d10, D(v,0.1)
Cumulative volume at 50%: d50, D(v,0.5)
Cumulative volume at 90%: d90, D(v,0.9)
P57 inicial: ubiquinone
P57-III: Ubiquinone:4-hydroxybenzoic acid cocrystal (1:1)
P57-V: Ubiquinone:resorcinol cocrystal (2:1)
P57-VI: Ubiquinone:hydroquinone (2:1)
P57-VII: Ubiquinone:orcinol cocrystal (2:3)
P57-VII: Ubiquinone:phloroglucinol monohydrate cocrystal (2:1:1)

Methodology

Particle size analysis (granulometry) was performed by laser dispersion on a Beckman Coulter LS13320 provided with a MLM (Micro Liquid Module) (measure range: 0.4 to 2000 µm; optic model: Fraunhofer.rdf, PIDS included).

In a beaker about 10 ml of silicone oil and a microspoon of sample were placed. The sample was homogeneized by pipetting it repeatedly with a pasteurized pipette and by subjecting it to ultrasonic treatment (30 KHz; 200 W). The module was cleaned and filled with silicone oil as a dispersing fluid. Before each analysis, an optical alignment of the laser and a measure of the instrument noise was made. Then, the sample was added to the analyzer until an obscuration between 8 and 12% was reached and the measurement was performed.

Analysis Conditions

Dispersing fluid: Silicone oil
Time before the first measurement: 0 s
Time of measurement: 5 s
Number of measures: 3
Time between measures: 0 s
Speed of the agitator: 51%
Obscuration: Standard
Optical model: Fraunhofer.rfd

Results

Table 8 show the summary of the obtained results of the particle size distribution of the samples analyzed.

TABLE 8

| Sample | Mean μm | SD | Mode μm | D10 μm | D50 μm | D90 μm |
|---|---|---|---|---|---|---|
| P57 inicial | 26.0 | 13.0 | 38.0 | 5.19 | 28.4 | 41.7 |
| P57 III | 19.0 | 12.4 | 34.6 | 2.51 | 18.2 | 36.1 |
| P57 V | 14.5 | 11.5 | 31.5 | 2.06 | 10.9 | 32.2 |
| P57 VI | 17.2 | 13.0 | 31.5 | 1.69 | 17.0 | 34.6 |
| P57 VII | 20.9 | 12.1 | 31.5 | 2.09 | 23.5 | 35.5 |
| P57 VIII | 22.0 | 9.26 | 31.5 | 9.46 | 22.2 | 34.0 |

Most of the sample population was between 9 and 60 μm of diameter (Table 9) with a mode diameter between 31.5 and 38 μm.

TABLE 9

Percentage of particles between 9.82 μm and 57.8 μm

| Sample | particles % |
|---|---|
| P57 inicial | 83.1 |
| P57 III | 70.5 |
| P57 V | 52.9 |
| P57 VI | 58.3 |
| P57 VII | 75.5 |
| P57 VIII | 88.9 |

It is observed that all the new reported solid forms have essentially an average particle size of the same order of magnitude than ubiquinone used for comparison ("P57 inicial" in table 9), and that most of the particles are between 9 and 60 μm.

Example 9.—Dissolution Rate of Ubiquinone vs Cocrystals

The dissolution rate of ubiquinone and of four of its co-crystals crystals obtained as in examples above was evaluated in FaSSIF-v2 medium (aqueous solution containing 106 mM sodium chloride, 28.4 mM monobasic sodium phosphate and 8.7 mM sodium hydroxide, adjusted with sodium hydroxide to pH 6.50), where maleic acid has been substituted by phosphoric acid.

Table 10 below shows the code, coformer, and stoichiometric ratio of the crystalline forms.

TABLE 10

| Code | Coformer | Stoichiometric ratio [ubiquinone:coformer:water] |
|---|---|---|
| P57 | | |
| P57-III | 4-Hydroxybenzoic acid (4HBA) | [1:1] |
| P57-V | Resorcinol | [1:1] |
| P57-VII | Orcinol | [2:3] |
| P57-VIII | Phloroglucinol | [2:1:1] |

1. Dissolution Rate Experiments

Tablet production: tablets of 8 mm diameter were made using a manual hydraulic tablet press (Applied Measurements Ltd, UK) up to a compression weight of 70 Kg. 40-50 mg of compound, ubiquinone or co-crystal, were weighted. The total exposed surface area was 0.5 $cm^2$.

Medium: aqueous solution containing 106 mM sodium chloride, 28.4 mM monobasic sodium phosphate, and 8.7 mM sodium hydroxide, adjusted with sodium hydroxide to pH 6.50.

Dissolution tests were performed with a small-scale dissolution assay installed in a GlpKa™ titrator (Sirius Analytical Instruments, UK).

Dissolution time and temperature: 2 hours and 25° C.

Procedure: 15 mL of aqueous medium was added into the sample vial containing the tablet. Spectra were recorded every 30 seconds for 1 hour through Sirius D-PAS spectrometer, with a bifurcated optic fibre dip probe (Hellma Analytics). The medium was stirred at a constant rate.

2. HPLC-MS/MS Quantification

HPLC conditions:
  Instrument: Agilent HPLC, consisting on two pumps, oven, and an autoinjector.
  Column: Teknokroma C8, 150×4.6 mm, 5 μm.
  Mobile phase: 5 mM ammonium formate in methanol: isopropanol (90:10).
  Elution mode: isocratic.
  Column temperature: 35° C.
  Flow rate: 1 mL/min.
  Injection volume: 10 mL.
  Retention time of ubiquinone: 8.5 min.

MS conditions:
  Instrument: Linear Ion Trap Quadrupole LC/MS/MS Mass Spectrometer 6500 Q TRAP (AB SCIEX Instruments).
  Curtain Gas: 25 p.s.i.
  Source temperature: 400° C.
  Ion Source Gas 1: 50 p.s.i.
  Ion Source Gas 2: 50 p.s.i.
  Ion Spray Voltage: 5500 V.
  Mode: positive ionization.
  Scan mode: MRM.
  Transitions for ubiquinone:
    Quantification: 880.8 (Q1)—197.1 (Q3); DP=100, CE=25; Dwell time=1000 ms.
    Confirmation: 880.8 (Q1)—149.3 (Q3); DP=90, CE=45; Dwell time=1000 ms.

Results

Dissolution rates of the cocrystals were determined by monitoring the dissolution profile of the different coformers. Molar extinction coefficients (MEC) of the coformers were measured in water, assuming that they would be nearly identical in FaSSIF aqueous solution.

Dissolution rate of ubiquinone was determined spectrophotometrically. However, as MEC of ubiquinone couldn't be determined in water due to the low solubility of the compound in this medium, concentration of ubiquinone in the dissolution profile was determined by HPLC-MS/MS.

Noyes-Whitney first order exponential equation was fitted to experimental points, providing the dissolution rate values shown in Table 11 below.

TABLE 11

| Compound | Dissolution rate (μg/min) |
|---|---|
| P57 | 0.0012 ± 0.0007 |
| P57-III | 56 ± 8 |
| P57-V | 5.7 ± 0.8 |
| P57-VII | 106 ± 23 |
| P57-VIII | 3.5 ± 0.4 |

Figure 15:
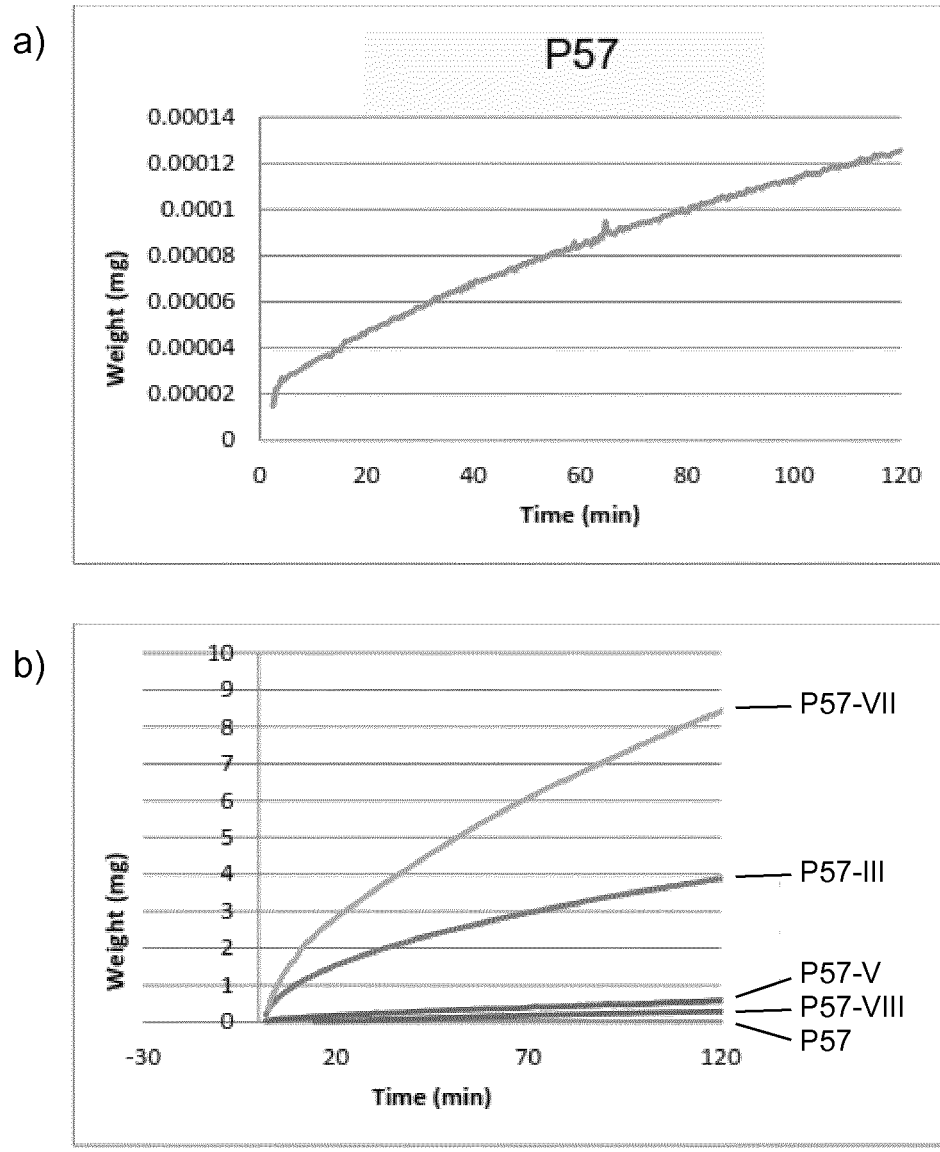
FIG. 15 shows the dissolution rate curve for a) ubiquinone (P57) and b) the comparison between dissolution rate curves of ubiquinona (P57), ubiquinone:4-hydroxybenzoic acid cocrystal (1:1) (P57-III), ubiquinone:resorcinol cocrystal (2:1) (P57-V), ubiquinone:orcinol cocrystal (2:3) (P57-VII), and ubiquinone:phloroglucinol monohydrate cocrystal (2:1:1) (P57-VIII).

A representative dissolution rate curve for a) ubiquinone (P57) and then b) the comparison between dissolution rate curves of the compounds listed in Table 11 is shown in FIG. 15.

All cocrystals dissolved faster than ubiquinone, being the cocrystals of orcinol (P57-VII) and 4-hydroxybenzoic acid (P57-III) the ones with the highest dissolution rate.

The invention claimed is:

1. A cocrystal of ubiquinone and a phenolic compound, wherein the phenolic compound is:
   1) 4-hydroxybenzoic acid, and which is characterized by having an X-ray powder diffractogram that comprises characteristic peaks at 1.4 and 2.8±0.3 degrees 2 theta with Cu—$K_\alpha$ radiation, $\lambda$=1.5418 Å;
   2) hydroquinone, and which is characterized by having an X-ray powder diffractogram that comprises characteristic peaks at 1.5 and 3.0±0.3 degrees 2 theta with Cu—$K_\alpha$ radiation, $\lambda$=1.5418 Å;
   3) hydroquinone and which is in the form of a benzyl alcohol solvate, characterized by having an X-ray powder diffractogram that comprises characteristic peaks at 1.4, 2.9±0.3 degrees 2 theta with Cu—$K_\alpha$ radiation, $\lambda$=1.5418 Å;
   4) orcinol, and which is characterized by having an X-ray powder diffractogram that comprises characteristic peaks at 1.5, 3.1±0.3 degrees 2 theta with Cu—$K_\alpha$ radiation, $\lambda$=1.5418 Å;
   5) Orcinol, and which is in the form of a benzyl alcohol solvate, characterized by having an X-ray powder diffractogram that comprises characteristic peaks at 12.9, 13.6±0.3 degrees 2 theta with Cu—$K_\alpha$ radiation, $\lambda$=1.5418 Å;
   6) phloroglucinol, and which is characterized by having an X-ray powder diffractogram that comprises characteristic peaks at 1.5, 3.0±0.3 degrees 2 theta with Cu—$K_\alpha$ radiation, $\lambda$=1.5418 Å;
   7) resorcinol, and which is characterized by having an X-ray powder diffractogram that comprises characteristic peaks at 1.5, 3.0±0.3 degrees 2 theta with Cu—$K_\alpha$ radiation, $\lambda$=1.5418 Å; or
   8) 2,4-dihydroxybenzoic acid, and which is characterized by having an X-ray powder diffractogram that comprises characteristic peaks at approximately 1.4 and 18.7±0.3 degrees 2 theta with Cu—$K_\alpha$ radiation, $\lambda$=1.5418 Å.

2. The cocrystal according to claim 1, have a particle size distribution wherein $D_{90}$ is equal to or lower than 45 µm.

3. The cocrystal according to claim 1, which have a particle size distribution wherein $D_{50}$ is equal to or lower than 30 µm.

4. The cocrystal according to claim 1, have a particle size distribution wherein $D_{10}$ is equal to or lower than 10 µm.

5. A composition comprising an effective amount of the cocrystal of ubiquinone and a phenolic compound as defined in claim 1 together with one or more appropriate acceptable excipients or carriers.

6. The composition according to claim 5, which is a pharmaceutical composition or a dietary supplement.

7. A method for the prophylaxis, for the treatment or both of a mammal suffering, or susceptible to suffer, from CoQ10 deficiencies, gingivitis, heart failure, angina, mitochondrial disorders, fibromyalgia, cardiovascular disease, atherosclerosis, dyslipidemia, hypertension, diabetes, cancer, infertility, and neurodegenerative diseases such as Parkinson's disease, Huntington's disease, Alzheimer's disease, and Friedreich's ataxia, wherein the method comprises administering to said mammal an effective amount of the cocrystal according to claim 1, together with one or more acceptable excipients or carriers.

* * * * *